(12) United States Patent
Pauls et al.

(10) Patent No.: US 11,725,043 B2
(45) Date of Patent: Aug. 15, 2023

(54) ULINASTATIN POLYPEPTIDES

(71) Applicant: DiaMedica USA Inc., Minneapolis, MN (US)

(72) Inventors: Rick Pauls, Minneapolis, MN (US); Todd Verdoorn, Minnetonka, MN (US); Karl Frank Johnson, Waunakee, WI (US); Gregory Thomas Bleck, Cross Plains, WI (US)

(73) Assignee: DiaMedica USA Inc., Minneapolis, MN (US)

( * ) Notice: Subject to any disclaimer, the term of this patent is extended or adjusted under 35 U.S.C. 154(b) by 46 days.

(21) Appl. No.: 17/193,481

(22) Filed: Mar. 5, 2021

(65) Prior Publication Data

US 2021/0277090 A1    Sep. 9, 2021

Related U.S. Application Data

(60) Provisional application No. 62/985,499, filed on Mar. 5, 2020, provisional application No. 63/021,938, filed on May 8, 2020, provisional application No. 63/108,773, filed on Nov. 2, 2020.

(51) Int. Cl.
| | |
|---|---|
| *A61K 38/57* | (2006.01) |
| *C07K 14/81* | (2006.01) |
| *C07K 14/76* | (2006.01) |
| *A61P 1/18* | (2006.01) |
| *A61P 29/00* | (2006.01) |
| *A61K 38/00* | (2006.01) |

(52) U.S. Cl.
CPC ............. *C07K 14/81* (2013.01); *A61K 38/57* (2013.01); *A61P 1/18* (2018.01); *A61P 29/00* (2018.01); *C07K 14/76* (2013.01); *C07K 14/8114* (2013.01); *A61K 38/00* (2013.01); *C07K 2319/31* (2013.01)

(58) Field of Classification Search
CPC ........ A61K 38/55; A61K 38/57; C07K 14/81; C07K 14/8114
See application file for complete search history.

(56) References Cited

U.S. PATENT DOCUMENTS

| | | |
|---|---|---|
| 4,950,465 A | 8/1990 | Sato et al. |
| 5,116,964 A | 5/1992 | Capon et al. |
| 5,407,915 A | 4/1995 | Fritz et al. |
| 5,409,895 A | 4/1995 | Morishita et al. |
| 5,428,130 A | 6/1995 | Capon et al. |
| 5,455,165 A | 10/1995 | Capon et al. |
| 5,514,582 A | 5/1996 | Capon et al. |
| 5,650,394 A | 7/1997 | Terao et al. |
| 5,777,081 A | 7/1998 | Michalski et al. |
| 5,783,555 A | 7/1998 | Suzuki et al. |
| 5,792,629 A | 8/1998 | Morishita et al. |
| 6,068,995 A | 5/2000 | Kobayashi et al. |
| 6,291,212 B1 | 9/2001 | Sledziewski et al. |
| 6,300,099 B1 | 10/2001 | Sledziewski et al. |
| 6,406,697 B1 | 6/2002 | Capon et al. |
| 6,509,445 B1 | 1/2003 | Kobayashi et al. |
| 6,583,108 B1 | 6/2003 | Tamburini et al. |
| 7,019,123 B2 | 3/2006 | Tamburini et al. |
| 7,452,859 B2 | 11/2008 | Tamburini et al. |
| 7,470,666 B2 | 12/2008 | Fu et al. |
| 9,856,310 B2 | 1/2018 | Chamberlain et al. |
| 10,351,618 B2 | 7/2019 | Chamberlain et al. |
| 2007/0275879 A1 | 11/2007 | Fu et al. |
| 2009/0298771 A1 | 12/2009 | Onichtchouk et al. |
| 2012/0238727 A1 | 9/2012 | Bleck et al. |
| 2016/0362475 A1 | 12/2016 | Chamberlain et al. |
| 2018/0072795 A1 | 3/2018 | Chamberlain et al. |
| 2022/0242932 A1* | 8/2022 | Pauls ..................... C07K 14/76 |

FOREIGN PATENT DOCUMENTS

| | | |
|---|---|---|
| CN | 103044554 A | 4/2013 |
| CN | 106924740 A | 7/2017 |
| EP | 0738516 A1 | 10/1996 |
| EP | 1060748 A1 | 12/2000 |
| JP | 2013-253079 A | 12/2013 |
| WO | WO 1995/011260 A1 | 4/1995 |
| WO | WO 1996/003503 A1 | 2/1996 |
| WO | WO 1996/012816 A1 | 5/1996 |
| WO | WO 1996/014085 A1 | 5/1996 |
| WO | WO 1996/020278 A2 | 7/1996 |
| WO | WO 1996/020726 A1 | 7/1996 |
| WO | WO 1996/026273 A1 | 8/1996 |
| WO | WO 1997/025422 A1 | 7/1997 |
| WO | WO 1999/043347 A1 | 9/1999 |
| WO | WO 1999/049076 A1 | 9/1999 |
| WO | WO 2000/045175 A1 | 8/2000 |
| WO | WO 2004/103399 A1 | 12/2004 |
| WO | WO 2011/008682 A1 | 1/2011 |
| WO | WO 2013/110026 A1 | 7/2013 |
| WO | WO 2015/127391 A1 | 8/2015 |
| WO | WO 2020/106881 A1 | 5/2020 |
| WO | WO-2021178843 A1 | 9/2021 |

OTHER PUBLICATIONS

ClinicalTrials.gov: "A Multi-Center, Randomized, Double-Blind, Placebo Controlled Study of the Safety and Efficacy of Ulinastatin for the Treatment of COVID-19 in Hospitalized Patients," May 19, 2020, 7 pages, Retrieved from the Internet: URL: https://clinicaltrials.gov/ct2/show/NCT04393311.

Dittrich, et al., Elastase activity on sputum neutrophils correlates with severity of lung disease in cystic fibrosis, European Respiratory Journal, 2018, 11 pages, vol. 51.

International Search Report and Written Opinion for International Application No. PCT/US2022/014095, dated Apr. 28, 2022, 13 pages.

(Continued)

*Primary Examiner* — Jeffrey E. Russel
(74) *Attorney, Agent, or Firm* — Cooley LLP

(57) ABSTRACT

Provided are ulinastatin glycoforms, ulinastatin fusion polypeptides, and related compositions, mixtures, and methods of use, including methods of recombinantly producing ulinastatin polypeptides and treating diseases.

27 Claims, 10 Drawing Sheets

Specification includes a Sequence Listing.

(56) References Cited

OTHER PUBLICATIONS

Ju, M., et al., "Ulinastatin ameliorates LPS-induced pulmonary inflammation and injury by blocking the MAPK/NF-κB signaling pathways in rats," Molecular Medicine Reports, Oct. 2019, vol. 20(4), pp. 3347-3354.

Leng, Y., et al., "Ulinastatin for Acute Lung Injury and Acute Respiratory Distress Syndrome: a Systematic Review and Meta-analysis," World Journal of Critical Care Medicine, Feb. 2014, vol. 3(1), pp. 34-41.

Liu, et al., A critical role for neutrophil elastase in experimental bullous pemphigoid, J Clin Invest., 2000, pp. 113-123, vol. 105, No. 1.

Maratea et al., "Deletion and fusion analysis of the phage phi X174 lysis gene E," Gene. 1985;40(1):39-46.

Meng, W., et al., "Ulinastatin: A Potential Alternative to Glucocorticoid in the Treatment of Severe Decompression Sickness," Frontiers in Physiology, Mar. 2020, vol. 11, p. 273.

Stanford University, Ulinastatin for the treatment of Covid-19 in hospitalized patients, May 19, 2020, 1 page.

Zhang, X., et al. "Ulinastatin Treatment for Acute Respiratory Distress Syndrome in China: a Meta-analysis of Randomized Controlled Trials," BMC Pulmonary Medicine, Nov. 2019, vol. 19(1), p. 196.

Atal, S. and Atal, S., "Ulinastatin—a newer potential therapeutic option for multiple organ dysfunction syndrome". J Basic Clin Physiol Pharmacol (Mar. 2016); 27(2): 91-99.

Chen, et al., "Safety and tolerability of high-dose ulinastatin after 2-hour intravenous infusion in adult healthy Chinese volunteers: A randomized double-blind, placebo-controlled ascending dose study". PLOS One (2016); 12(5): e0177425.

Delaria, et al., "Characterization of Placental Bikunin, a Novel Human Serine Protease Inhibitor". The Journal of Biological Chemistry (1997); 272(18): 12209-12214.

Desjarlais and Berg, "Use of a zinc-finger consensus sequence framework and specificity rules to design specific DNA binding proteins". PNAS (Mar. 1993); 90: 2256-2260.

Desjarlais and Berg, "Length-encoded multiplex binding site determination: Application to zinc finger proteins". PNAS (Nov. 1996); 91: 11099-11103.

Inoue, K. and Takano, H., "Urinary Trypsin Inhibitor, an Alternative Therapeutic Option for Inflammatory Disorders", Inflammatory Diseases—A Modern Perspective (2011); Dr. Amit Nagal (Ed.), Ch. 1, pp. 1-14, 15 pages, ISBN: 978-953-307-444-3, InTech, Available from: http://www.intechopen.com/books/inflammatory-diseases-a-modernperspective/urinary-trypsin-inhibitor-an-alternative-therapeutic-option-for-inflammatory-disorders.

Invitation to Pay Additional Fees for International Application No. PCT/US2021/021148 mailed May 18, 2021, 2 pages.

International Preliminary Report on Patentability for International Application No. PCT/US2019/062471 dated May 25, 2021, 7 pages.

International Search Report and Written Opinion for International Application No. PCT/US2019/062471 dated Feb. 20, 2020, 10 pages.

Karnad, et al., "Intravenous administration of Ulinastatin (human urinary trypsin inhibitor) in severe sepsis: a multicenter randomized controlled study". Intensive Care Med (Jun. 2014); 40(6): 830-838. Epub Apr. 16, 2014.

Marlor, et al., "Identification and Cloning of Human Placental bikunin, a novel serine protease inhibitor containing two kunitz domains". The Journal of Biological Chemistry (1997); 272(18): 12201-12208.

Nakamura, et al., "Codon usage tabulated from international DNA sequence databases: status for the year 2000". Nucleic Acids Research (2000); 28(1): 292, 1 page.

Nakamura, et al., "Characterization of a novel variant of the second domain of bikunin with increased leukocyte elastase inhibitory activity". Journal of Biophysical Chemistry (2012); 3(2): 132-141.

Polverino, et al., "The Role of Neutrophil Elastase Inhibitors in Lung Diseases". Chest (Aug. 2017); 152(2): 249-262. Epub Apr. 23, 2017.

Pugia, et al., "Bikunin (urinary Trypsin Inhibitor): structure, biological relevance and measurement". Adv Clin Chem. (2007); 44: 223-245, 23 pages.

Ryan and Flint, "Virus-encoded proteinases of the picornavirus super-group". Journal of General Virology (1997); 78: 699-723.

Wei, et al., "Anti-inflammatory mechanisms of ulinastatin: Inhibiting the hyperpermeability of vascular endothelial cells induced by TNF-α via the RhoA/ROCK signal pathway". International Immunopharmacology (2017); 46: 220-227.

Zheng, et al., "A meta-analysis on the effect of ulinastatin on serum levels of C-reactive protein, interleukin 6 and tumor necrosis factor alpha in Asian patients with acute pancreatitis". Genetic Testing and Molecular Biomarkers (2016); 20(3): 118-124.

* cited by examiner

SEQUENCE LISTING

<160> NUMBER OF SEQ ID NOS: 70

<210> SEQ ID NO 1
<211> LENGTH: 333
<212> TYPE: PRT
<213> ORGANISM: Homo sapiens

<400> SEQUENCE: 1

```
Gly Pro Val Pro Ala Pro Pro Asp Asn Ile Gln Val Gln Glu Asn Phe
1               5                   10                  15

Asn Ile Ser Arg Ile Tyr Gly Lys Trp Tyr Asn Leu Ala Ile Gly Ser
            20                  25                  30

Thr Cys Pro Trp Leu Lys Lys Ile Met Asp Arg Met Thr Val Ser Thr
        35                  40                  45

Leu Val Leu Gly Glu Gly Ala Thr Glu Ala Glu Ile Ser Met Thr Ser
    50                  55                  60

Thr Arg Trp Arg Lys Gly Val Cys Glu Glu Thr Ser Gly Ala Tyr Glu
65                  70                  75                  80

Lys Thr Asp Thr Asp Gly Lys Phe Leu Tyr His Lys Ser Lys Trp Asn
                85                  90                  95

Ile Thr Met Glu Ser Tyr Val Val His Thr Asn Tyr Asp Glu Tyr Ala
            100                 105                 110

Ile Phe Leu Thr Lys Lys Phe Ser Arg His His Gly Pro Thr Ile Thr
            115                 120                 125

Ala Lys Leu Tyr Gly Arg Ala Pro Gln Leu Arg Glu Thr Leu Leu Gln
        130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175

Glu Pro Ile Leu Ile Pro Arg Val Arg Arg Ala Val Leu Pro Gln Glu
            180                 185                 190

Glu Glu Gly Ala Gly Gly Gln Leu Val Thr Glu Val Thr Lys Lys
        195                 200                 205

Glu Asp Ser Cys Gln Leu Gly Tyr Ser Ala Gly Pro Cys Met Gly Met
    210                 215                 220

Thr Ser Arg Tyr Phe Tyr Asn Gly Thr Ser Met Ala Cys Glu Thr Phe
225                 230                 235                 240

Gln Tyr Gly Gly Cys Met Gly Asn Gly Asn Asn Phe Val Thr Glu Lys
                245                 250                 255

Glu Cys Leu Gln Thr Cys Arg Thr Val Ala Ala Cys Asn Leu Pro Ile
            260                 265                 270

Val Arg Gly Pro Cys Arg Ala Phe Ile Gln Leu Trp Ala Phe Asp Ala
275                 280                 285

Val Lys Gly Lys Cys Val Leu Phe Pro Tyr Gly Gly Cys Gln Gly Asn
        290                 295                 300

Gly Asn Lys Phe Tyr Ser Glu Lys Glu Cys Arg Glu Tyr Cys Gly Val
305                 310                 315                 320

Pro Gly Asp Gly Asp Glu Glu Leu Leu Arg Phe Ser Asn
                325                 330

<210> SEQ ID NO 2
<211> LENGTH: 147
<212> TYPE: PRT
<213> ORGANISM: Homo sapiens

<400> SEQUENCE: 2

Ala Val Leu Pro Gln Glu Glu Glu Gly Ala Gly Gly Gln Leu Val
1               5                   10                  15

Thr Glu Val Thr Lys Lys Glu Asp Ser Cys Gln Leu Gly Tyr Ser Ala
            20                  25                  30

Gly Pro Cys Met Gly Met Thr Ser Arg Tyr Phe Tyr Asn Gly Thr Ser
        35                  40                  45
```

```
Met Ala Cys Glu Thr Phe Gln Tyr Gly Gly Cys Met Gly Asn Gly Asn
 50                  55                  60

Asn Phe Val Thr Glu Lys Glu Cys Leu Gln Thr Cys Arg Thr Val Ala
 65                  70                  75                  80

Ala Cys Asn Leu Pro Ile Val Arg Gly Pro Cys Arg Ala Phe Ile Gln
                 85                  90                  95

Leu Trp Ala Phe Asp Ala Val Lys Gly Lys Cys Val Leu Phe Pro Tyr
            100                 105                 110

Gly Gly Cys Gln Gly Asn Gly Asn Lys Phe Tyr Ser Glu Lys Glu Cys
        115                 120                 125

Arg Glu Tyr Cys Gly Val Pro Gly Asp Gly Asp Glu Glu Leu Leu Arg
    130                 135                 140

Phe Ser Asn
145

<210> SEQ ID NO 3
<211> LENGTH: 333
<212> TYPE: PRT
<213> ORGANISM: Homo sapiens

<400> SEQUENCE: 3

Gly Pro Val Pro Ala Pro Pro Asp Asn Ile Gln Val Gln Glu Asn Phe
1               5                   10                  15

Asn Ile Ser Arg Ile Tyr Gly Lys Trp Tyr Asn Leu Ala Ile Gly Ser
            20                  25                  30

Thr Cys Pro Trp Leu Lys Lys Ile Met Asp Arg Met Thr Val Ser Thr
        35                  40                  45

Leu Val Leu Gly Glu Gly Ala Thr Glu Ala Glu Ile Ser Met Thr Ser
    50                  55                  60

Thr Arg Trp Arg Lys Gly Val Cys Glu Glu Thr Ser Gly Ala Tyr Glu
65                  70                  75                  80

Lys Thr Asp Thr Asp Gly Lys Phe Leu Tyr His Lys Ser Lys Trp Asn
                85                  90                  95

Ile Thr Met Glu Ser Tyr Val Val His Thr Asn Tyr Asp Glu Tyr Ala
            100                 105                 110

Ile Phe Leu Thr Lys Lys Phe Ser Arg His His Gly Pro Thr Ile Thr
        115                 120                 125

Ala Lys Leu Tyr Gly Arg Ala Pro Gln Leu Arg Glu Thr Leu Leu Gln
    130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175

Glu Pro Ile Leu Ile Pro Arg Val Arg Arg Ala Val Leu Pro Gln Glu
            180                 185                 190

Glu Glu Gly Ser Gly Gly Gly Gln Leu Val Thr Glu Val Thr Lys Lys
        195                 200                 205

Glu Asp Ser Cys Gln Leu Gly Tyr Ser Ala Gly Pro Cys Met Gly Met
    210                 215                 220

Thr Ser Arg Tyr Phe Tyr Asn Gly Thr Ser Met Ala Cys Glu Thr Phe
225                 230                 235                 240

Gln Tyr Gly Gly Cys Met Gly Asn Gly Asn Asn Phe Val Thr Glu Lys
                245                 250                 255

Glu Cys Leu Gln Thr Cys Arg Thr Val Ala Ala Cys Asn Leu Pro Ile
```

```
                     260                 265                 270
Val Arg Gly Pro Cys Arg Ala Phe Ile Gln Leu Trp Ala Phe Asp Ala
            275                 280                 285

Val Lys Gly Lys Cys Val Leu Phe Pro Tyr Gly Gly Cys Gln Gly Asn
            290                 295                 300

Gly Asn Lys Phe Tyr Ser Glu Lys Glu Cys Arg Glu Tyr Cys Gly Val
305                 310                 315                 320

Pro Gly Asp Gly Asp Glu Glu Leu Leu Arg Phe Ser Asn
            325                 330

<210> SEQ ID NO 4
<211> LENGTH: 147
<212> TYPE: PRT
<213> ORGANISM: Homo sapiens

<400> SEQUENCE: 4

Ala Val Leu Pro Gln Glu Glu Gly Ser Gly Gly Gly Gln Leu Val
1               5                   10                  15

Thr Glu Val Thr Lys Lys Glu Asp Ser Cys Gln Leu Gly Tyr Ser Ala
                20                  25                  30

Gly Pro Cys Met Gly Met Thr Ser Arg Tyr Phe Tyr Asn Gly Thr Ser
            35                  40                  45

Met Ala Cys Glu Thr Phe Gln Tyr Gly Gly Cys Met Gly Asn Gly Asn
50                  55                  60

Asn Phe Val Thr Glu Lys Glu Cys Leu Gln Thr Cys Arg Thr Val Ala
65                  70                  75                  80

Ala Cys Asn Leu Pro Ile Val Arg Gly Pro Cys Arg Ala Phe Ile Gln
                85                  90                  95

Leu Trp Ala Phe Asp Ala Val Lys Gly Lys Cys Val Leu Phe Pro Tyr
            100                 105                 110

Gly Gly Cys Gln Gly Asn Gly Asn Lys Phe Tyr Ser Glu Lys Glu Cys
        115                 120                 125

Arg Glu Tyr Cys Gly Val Pro Gly Asp Gly Asp Glu Glu Leu Leu Arg
    130                 135                 140

Phe Ser Asn
145

<210> SEQ ID NO 5
<211> LENGTH: 19
<212> TYPE: PRT
<213> ORGANISM: Bos Taurus

<400> SEQUENCE: 5

Met Met Ser Phe Val Ser Leu Leu Leu Val Gly Ile Leu Phe His Ala
1               5                   10                  15

Thr Gln Ala

<210> SEQ ID NO 6
<211> LENGTH: 352
<212> TYPE: PRT
<213> ORGANISM: Artificial Sequence
<220> FEATURE:
<223> OTHER INFORMATION: Made in Lab - FL Human Ulinastatin S10A
      Mutation with Signal Sequence Fusion Polypeptide

<400> SEQUENCE: 6

Met Met Ser Phe Val Ser Leu Leu Leu Val Gly Ile Leu Phe His Ala
1               5                   10                  15
```

Thr Gln Ala Gly Pro Val Pro Ala Pro Asp Asn Ile Gln Val Gln
            20                  25                  30

Glu Asn Phe Asn Ile Ser Arg Ile Tyr Gly Lys Trp Tyr Asn Leu Ala
            35                  40                  45

Ile Gly Ser Thr Cys Pro Trp Leu Lys Lys Ile Met Asp Arg Met Thr
50                  55                  60

Val Ser Thr Leu Val Leu Gly Glu Gly Ala Thr Glu Ala Glu Ile Ser
65                  70                  75                  80

Met Thr Ser Thr Arg Trp Arg Lys Gly Val Cys Glu Glu Thr Ser Gly
                85                  90                  95

Ala Tyr Glu Lys Thr Asp Thr Asp Gly Lys Phe Leu Tyr His Lys Ser
            100                 105                 110

Lys Trp Asn Ile Thr Met Glu Ser Tyr Val Val His Thr Asn Tyr Asp
            115                 120                 125

Glu Tyr Ala Ile Phe Leu Thr Lys Lys Phe Ser Arg His His Gly Pro
            130                 135                 140

Thr Ile Thr Ala Lys Leu Tyr Gly Arg Ala Pro Gln Leu Arg Glu Thr
145                 150                 155                 160

Leu Leu Gln Asp Phe Arg Val Val Ala Gln Gly Val Gly Ile Pro Glu
            165                 170                 175

Asp Ser Ile Phe Thr Met Ala Asp Arg Gly Glu Cys Val Pro Gly Glu
            180                 185                 190

Gln Glu Pro Glu Pro Ile Leu Ile Pro Arg Val Arg Arg Ala Val Leu
            195                 200                 205

Pro Gln Glu Glu Glu Gly Ala Gly Gly Gly Gln Leu Val Thr Glu Val
210                 215                 220

Thr Lys Lys Glu Asp Ser Cys Gln Leu Gly Tyr Ser Ala Gly Pro Cys
225                 230                 235                 240

Met Gly Met Thr Ser Arg Tyr Phe Tyr Asn Gly Thr Ser Met Ala Cys
                245                 250                 255

Glu Thr Phe Gln Tyr Gly Gly Cys Met Gly Asn Gly Asn Asn Phe Val
            260                 265                 270

Thr Glu Lys Glu Cys Leu Gln Thr Cys Arg Thr Val Ala Ala Cys Asn
            275                 280                 285

Leu Pro Ile Val Arg Gly Pro Cys Arg Ala Phe Ile Gln Leu Trp Ala
            290                 295                 300

Phe Asp Ala Val Lys Gly Lys Cys Val Leu Phe Pro Tyr Gly Gly Cys
305                 310                 315                 320

Gln Gly Asn Gly Asn Lys Phe Tyr Ser Glu Lys Glu Cys Arg Glu Tyr
            325                 330                 335

Cys Gly Val Pro Gly Asp Gly Asp Glu Glu Leu Leu Arg Phe Ser Asn
            340                 345                 350

<210> SEQ ID NO 7
<211> LENGTH: 166
<212> TYPE: PRT
<213> ORGANISM: Artificial Sequence
<220> FEATURE:
<223> OTHER INFORMATION: Made in Lab - Mature Human Ulinastatin S10A
      Mutation with Signal Sequence Fusion Polypeptide

<400> SEQUENCE: 7

Met Met Ser Phe Val Ser Leu Leu Leu Val Gly Ile Leu Phe His Ala
1               5                   10                  15

Thr Gln Ala Ala Val Leu Pro Gln Glu Glu Glu Gly Ala Gly Gly Gly
            20                  25                  30

```
Gln Leu Val Thr Glu Val Thr Lys Lys Glu Asp Ser Cys Gln Leu Gly
             35                  40                  45

Tyr Ser Ala Gly Pro Cys Met Gly Met Thr Ser Arg Tyr Phe Tyr Asn
     50                  55                  60

Gly Thr Ser Met Ala Cys Glu Thr Phe Gln Tyr Gly Gly Cys Met Gly
 65                  70                  75                  80

Asn Gly Asn Asn Phe Val Thr Glu Lys Glu Cys Leu Gln Thr Cys Arg
                 85                  90                  95

Thr Val Ala Ala Cys Asn Leu Pro Ile Val Arg Gly Pro Cys Arg Ala
            100                 105                 110

Phe Ile Gln Leu Trp Ala Phe Asp Ala Val Lys Gly Lys Cys Val Leu
            115                 120                 125

Phe Pro Tyr Gly Gly Cys Gln Gly Asn Gly Asn Lys Phe Tyr Ser Glu
        130                 135                 140

Lys Glu Cys Arg Glu Tyr Cys Gly Val Pro Gly Asp Gly Asp Glu Glu
145                 150                 155                 160

Leu Leu Arg Phe Ser Asn
            165

<210> SEQ ID NO 8
<211> LENGTH: 1059
<212> TYPE: DNA
<213> ORGANISM: Artificial Sequence
<220> FEATURE:
<223> OTHER INFORMATION: Made in Lab - FL Human Ulinastatin S10A
      Mutation with Signal Sequence coding polynucleotide

<400> SEQUENCE: 8
atgatgtcct ttgtctctct gctcctggtt ggcatcctat tccatgccac ccaggccggc      60
cctgtgccag ctccgcccga acatccaa gtgcaggaaa acttcaatat ctctcggatc     120
tatgggaagt ggtacaacct ggccatcggt tccacctgcc cctggctgaa gaagatcatg     180
gacaggatga cagtgagcac gctggtgctg ggagagggcg ctacagaggc ggagatcagc     240
atgacaagca ctcgttggcg gaaaggtgtc tgtgaggaga cgtctggagc ttatgagaaa     300
acagatactg acgggaagtt tctctatcac aaatccaaat ggaatataac catggagtcc     360
tatgtggtcc acaccaacta tgatgagtat gccattttcc tgacaaagaa attcagccgc     420
catcacggac ccaccattac tgccaagctc tacgggcggg cgccgcagct gagggaaact     480
ctcctgcagg acttcagagt ggttgcccag ggtgtgggca tccctgagga ctccatcttc     540
accatggctg accgaggcga atgtgtccca ggggagcagg aaccagagcc atcttaatc     600 ccgagagtcc ggagggctgt gctaccccaa gaagaggaag agctggggg tgggcaactg     660 gtaactgaag tcaccaagaa agaagattcc tgccagctgg gctactcggc cggtccctgt     720
atgggaatga ccagcagata tttctataat ggaacatcca tggcctgtga gactttccag     780
tacggcggct gcatgggaaa cggcaacaac ttcgtcacag aaaaggagtg tctgcagacc     840
tgccgaactg tggcggcctg caatctcccc atcgtccggg gcccctgccg agccttcatc     900
cagctctggg catttgatgc tgtcaagggg aagtgcgtcc tcttcccta cggggggctgc     960 cagggcaacg gaacaagtt ctactcagag aaggagtgca gagtactg cggtgtccct    1020 ggtgatggtg atgaggagct gctgcgcttc tccaactga                            1059

<210> SEQ ID NO 9
<211> LENGTH: 501
<212> TYPE: DNA
```

-continued

<213> ORGANISM: Artificial Sequence
<220> FEATURE:
<223> OTHER INFORMATION: Made in Lab - Mature Human Ulinastatin S10A
      Mutation with Signal Sequence coding polynucleotide

<400> SEQUENCE: 9

```
atgatgtcct ttgtctctct gctcctggtt ggcatcctat tccatgccac ccaggccgct    60
gtgctacccc aagaagagga aggagctggg ggtgggcaac tggtaactga agtcaccaag   120
aaagaagatt cctgccagct gggctactcg gccggtccct gtatgggaat gaccagcaga   180
tatttctata atggaacatc catggcctgt gagactttcc agtacggcgg ctgcatggga   240
aacggcaaca acttcgtcac agaaaaggag tgtctgcaga cctgccgaac tgtggcggcc   300
tgcaatctcc ccatcgtccg gggccccctgc cgagccttca tccagctctg gcatttgat   360 gctgtcaagg ggaagtgcgt cctcttcccc tacgggggct gccagggcaa cgggaacaag   420
ttctactcag agaaggagtg cagagagtac tgcggtgtcc ctggtgatgg tgatgaggag   480
ctgctgcgct ctccaactg a                                              501
```

<210> SEQ ID NO 10
<211> LENGTH: 4
<212> TYPE: PRT
<213> ORGANISM: Artificial Sequence
<220> FEATURE:
<223> OTHER INFORMATION: Linker sequence

<400> SEQUENCE: 10

Gly Gly Ser Gly
1

<210> SEQ ID NO 11
<211> LENGTH: 4
<212> TYPE: PRT
<213> ORGANISM: Artificial Sequence
<220> FEATURE:
<223> OTHER INFORMATION: Made in Lab - non-cleavable peptide linker

<400> SEQUENCE: 11

Gly Ser Gly Ser
1

<210> SEQ ID NO 12
<211> LENGTH: 4
<212> TYPE: PRT
<213> ORGANISM: Artificial Sequence
<220> FEATURE:
<223> OTHER INFORMATION: Made in Lab - non-cleavable peptide linker

<400> SEQUENCE: 12

Gly Gly Gly Ser
1

<210> SEQ ID NO 13
<211> LENGTH: 5
<212> TYPE: PRT
<213> ORGANISM: Artificial Sequence
<220> FEATURE:
<223> OTHER INFORMATION: Made in Lab - non-cleavable peptide linker

<400> SEQUENCE: 13

Gly Gly Gly Gly Ser
1               5

<210> SEQ ID NO 14

```
<211> LENGTH: 4
<212> TYPE: PRT
<213> ORGANISM: Artificial Sequence
<220> FEATURE:
<223> OTHER INFORMATION: Made in Lab - non-cleavable peptide linker

<400> SEQUENCE: 14

Gly Asn Gly Asn
1

<210> SEQ ID NO 15
<211> LENGTH: 4
<212> TYPE: PRT
<213> ORGANISM: Artificial Sequence
<220> FEATURE:
<223> OTHER INFORMATION: Made in Lab - non-cleavable peptide linker

<400> SEQUENCE: 15

Gly Gly Asn Gly
1

<210> SEQ ID NO 16
<211> LENGTH: 4
<212> TYPE: PRT
<213> ORGANISM: Artificial Sequence
<220> FEATURE:
<223> OTHER INFORMATION: Made in Lab - non-cleavable peptide linker

<400> SEQUENCE: 16

Gly Gly Gly Asn
1

<210> SEQ ID NO 17
<211> LENGTH: 5
<212> TYPE: PRT
<213> ORGANISM: Artificial Sequence
<220> FEATURE:
<223> OTHER INFORMATION: Made in Lab - non-cleavable peptide linker

<400> SEQUENCE: 17

Gly Gly Gly Gly Asn
1               5

<210> SEQ ID NO 18
<211> LENGTH: 15
<212> TYPE: PRT
<213> ORGANISM: Artificial Sequence
<220> FEATURE:
<223> OTHER INFORMATION: Made in Lab - non-cleavable peptide linker

<400> SEQUENCE: 18

Gly Gly Gly Gly Ser Gly Gly Gly Gly Ser Gly Gly Gly Gly Ser
1               5                   10                  15

<210> SEQ ID NO 19
<211> LENGTH: 22
<212> TYPE: PRT
<213> ORGANISM: Artificial Sequence
<220> FEATURE:
<223> OTHER INFORMATION: Made in Lab - non-cleavable peptide linker

<400> SEQUENCE: 19

Gly Ser Gly Gly Gly Gly Ser Gly Gly Gly Gly Ser Gly Gly Gly Gly
1               5                   10                  15

Ser Gly Gly Gly Gly Ser
            20
```

<210> SEQ ID NO 20
<211> LENGTH: 30
<212> TYPE: PRT
<213> ORGANISM: Artificial Sequence
<220> FEATURE:
<223> OTHER INFORMATION: Made in Lab - non-cleavable peptide linker

<400> SEQUENCE: 20

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 21
<211> LENGTH: 25
<212> TYPE: PRT
<213> ORGANISM: Artificial Sequence
<220> FEATURE:
<223> OTHER INFORMATION: Made in Lab - non-cleavable peptide linker

<400> SEQUENCE: 21

Asp Ala Ala Ala Lys Glu Ala Ala Ala Lys Asp Ala Ala Ala Arg Glu
1               5                   10                  15

Ala Ala Ala Arg Asp Ala Ala Ala Lys
            20                  25

<210> SEQ ID NO 22
<211> LENGTH: 14
<212> TYPE: PRT
<213> ORGANISM: Artificial Sequence
<220> FEATURE:
<223> OTHER INFORMATION: Made in Lab - non-cleavable peptide linker

<400> SEQUENCE: 22

Asn Val Asp His Lys Pro Ser Asn Thr Lys Val Asp Lys Arg
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Made in Lab - non-cleavable peptide linker

<400> SEQUENCE: 23

Asp Gly Gly Gly Ser
1               5

<210> SEQ ID NO 24
<211> LENGTH: 5
<212> TYPE: PRT
<213> ORGANISM: Artificial Sequence
<220> FEATURE:
<223> OTHER INFORMATION: Made in Lab - non-cleavable peptide linker

<400> SEQUENCE: 24

Thr Gly Glu Lys Pro
1               5

<210> SEQ ID NO 25
<211> LENGTH: 4
<212> TYPE: PRT
<213> ORGANISM: Artificial Sequence
<220> FEATURE:
<223> OTHER INFORMATION: Made in Lab - non-cleavable peptide linker

```
<400> SEQUENCE: 25

Gly Gly Arg Arg
1

<210> SEQ ID NO 26
<211> LENGTH: 14
<212> TYPE: PRT
<213> ORGANISM: Artificial Sequence
<220> FEATURE:
<223> OTHER INFORMATION: Made in Lab - non-cleavable peptide linker

<400> SEQUENCE: 26

Glu Gly Lys Ser Ser Gly Ser Gly Ser Glu Ser Lys Val Asp
1               5                   10

<210> SEQ ID NO 27
<211> LENGTH: 18
<212> TYPE: PRT
<213> ORGANISM: Artificial Sequence
<220> FEATURE:
<223> OTHER INFORMATION: Made in Lab - non-cleavable peptide linker

<400> SEQUENCE: 27

Lys Glu Ser Gly Ser Val Ser Ser Glu Gln Leu Ala Gln Phe Arg Ser
1               5                   10                  15

Leu Asp

<210> SEQ ID NO 28
<211> LENGTH: 8
<212> TYPE: PRT
<213> ORGANISM: Artificial Sequence
<220> FEATURE:
<223> OTHER INFORMATION: Made in Lab - non-cleavable peptide linker

<400> SEQUENCE: 28

Gly Gly Arg Arg Gly Gly Gly Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Made in Lab - non-cleavable peptide linker

<400> SEQUENCE: 29

Leu Arg Gln Arg Asp Gly Glu Arg Pro
1               5

<210> SEQ ID NO 30
<211> LENGTH: 12
<212> TYPE: PRT
<213> ORGANISM: Artificial Sequence
<220> FEATURE:
<223> OTHER INFORMATION: Made in Lab - non-cleavable peptide linker

<400> SEQUENCE: 30

Leu Arg Gln Lys Asp Gly Gly Gly Ser Glu Arg Pro
1               5                   10

<210> SEQ ID NO 31
<211> LENGTH: 16
<212> TYPE: PRT
<213> ORGANISM: Artificial Sequence
<220> FEATURE:
<223> OTHER INFORMATION: Made in Lab - non-cleavable peptide linker
```

<400> SEQUENCE: 31

Leu Arg Gln Lys Asp Gly Gly Gly Ser Gly Gly Gly Ser Glu Arg Pro
1               5                   10                  15

<210> SEQ ID NO 32
<211> LENGTH: 19
<212> TYPE: PRT
<213> ORGANISM: Artificial Sequence
<220> FEATURE:
<223> OTHER INFORMATION: Made in Lab - self cleaving polypeptide site

<400> SEQUENCE: 32

Leu Leu Asn Phe Asp Leu Leu Lys Leu Ala Gly Asp Val Glu Ser Asn
1               5                   10                  15

Pro Gly Pro

<210> SEQ ID NO 33
<211> LENGTH: 19
<212> TYPE: PRT
<213> ORGANISM: Artificial Sequence
<220> FEATURE:
<223> OTHER INFORMATION: Made in Lab - self cleaving polypeptide site

<400> SEQUENCE: 33

Thr Leu Asn Phe Asp Leu Leu Lys Leu Ala Gly Asp Val Glu Ser Asn
1               5                   10                  15

Pro Gly Pro

<210> SEQ ID NO 34
<211> LENGTH: 14
<212> TYPE: PRT
<213> ORGANISM: Artificial Sequence
<220> FEATURE:
<223> OTHER INFORMATION: Made in Lab - self cleaving polypeptide site

<400> SEQUENCE: 34

Leu Leu Lys Leu Ala Gly Asp Val Glu Ser Asn Pro Gly Pro
1               5                   10

<210> SEQ ID NO 35
<211> LENGTH: 17
<212> TYPE: PRT
<213> ORGANISM: Artificial Sequence
<220> FEATURE:
<223> OTHER INFORMATION: Made in Lab - self cleaving polypeptide site

<400> SEQUENCE: 35

Asn Phe Asp Leu Leu Lys Leu Ala Gly Asp Val Glu Ser Asn Pro Gly
1               5                   10                  15

Pro

<210> SEQ ID NO 36
<211> LENGTH: 20
<212> TYPE: PRT
<213> ORGANISM: Artificial Sequence
<220> FEATURE:
<223> OTHER INFORMATION: Made in Lab - self cleaving polypeptide site

<400> SEQUENCE: 36

Gln Leu Leu Asn Phe Asp Leu Leu Lys Leu Ala Gly Asp Val Glu Ser
1               5                   10                  15

Asn Pro Gly Pro
            20

```
<210> SEQ ID NO 37
<211> LENGTH: 24
<212> TYPE: PRT
<213> ORGANISM: Artificial Sequence
<220> FEATURE:
<223> OTHER INFORMATION: Made in Lab - self cleaving polypeptide site

<400> SEQUENCE: 37

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 38
<211> LENGTH: 40
<212> TYPE: PRT
<213> ORGANISM: Artificial Sequence
<220> FEATURE:
<223> OTHER INFORMATION: Made in Lab - self cleaving polypeptide site

<400> SEQUENCE: 38

Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr
        35                  40

<210> SEQ ID NO 39
<211> LENGTH: 18
<212> TYPE: PRT
<213> ORGANISM: Artificial Sequence
<220> FEATURE:
<223> OTHER INFORMATION: Made in Lab - self cleaving polypeptide site

<400> SEQUENCE: 39

Leu Asn Phe Asp Leu Leu Lys Leu Ala Gly Asp Val Glu Ser Asn Pro
1               5                   10                  15

Gly Pro

<210> SEQ ID NO 40
<211> LENGTH: 40
<212> TYPE: PRT
<213> ORGANISM: Artificial Sequence
<220> FEATURE:
<223> OTHER INFORMATION: Made in Lab - self cleaving polypeptide site

<400> SEQUENCE: 40

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 41
<211> LENGTH: 33
<212> TYPE: PRT
<213> ORGANISM: Artificial Sequence
<220> FEATURE:
<223> OTHER INFORMATION: Made in Lab - self cleaving polypeptide site

<400> SEQUENCE: 41
```

```
Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 42
<211> LENGTH: 7
<212> TYPE: PRT
<213> ORGANISM: Artificial Sequence
<220> FEATURE:
<223> OTHER INFORMATION: Cleavage sequence by TEV protease
<220> FEATURE:
<221> NAME/KEY: misc_feature
<222> LOCATION: (2)..(3)
<223> OTHER INFORMATION: Xaa is any amino acid
<220> FEATURE:
<221> NAME/KEY: misc_feature
<222> LOCATION: (5)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa = Gly or Ser

<400> SEQUENCE: 42

Glu Xaa Xaa Tyr Xaa Gln Xaa
1               5

<210> SEQ ID NO 43
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 43

Glu Asn Leu Tyr Phe Gln Gly
1               5

<210> SEQ ID NO 44
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 44

Glu Asn Leu Tyr Phe Gln Ser
1               5

<210> SEQ ID NO 45
<211> LENGTH: 4
<212> TYPE: PRT
<213> ORGANISM: Artificial Sequence
<220> FEATURE:
<223> OTHER INFORMATION: Made in Lab - cleavable peptide linker

<400> SEQUENCE: 45

Gly Arg Gly Asp
1

<210> SEQ ID NO 46
<211> LENGTH: 6
<212> TYPE: PRT
<213> ORGANISM: Artificial Sequence
<220> FEATURE:
```

```
<223> OTHER INFORMATION: Made in Lab - cleavable peptide linker

<400> SEQUENCE: 46

Gly Arg Gly Asp Asn Pro
1               5

<210> SEQ ID NO 47
<211> LENGTH: 5
<212> TYPE: PRT
<213> ORGANISM: Artificial Sequence
<220> FEATURE:
<223> OTHER INFORMATION: Made in Lab - cleavable peptide linker

<400> SEQUENCE: 47

Gly Arg Gly Asp Ser
1               5

<210> SEQ ID NO 48
<211> LENGTH: 7
<212> TYPE: PRT
<213> ORGANISM: Artificial Sequence
<220> FEATURE:
<223> OTHER INFORMATION: Made in Lab - cleavable peptide linker

<400> SEQUENCE: 48

Gly Arg Gly Asp Ser Pro Lys
1               5

<210> SEQ ID NO 49
<211> LENGTH: 4
<212> TYPE: PRT
<213> ORGANISM: Artificial Sequence
<220> FEATURE:
<223> OTHER INFORMATION: Made in Lab - cleavable peptide linker

<400> SEQUENCE: 49

Ala Ala Pro Val
1

<210> SEQ ID NO 50
<211> LENGTH: 4
<212> TYPE: PRT
<213> ORGANISM: Artificial Sequence
<220> FEATURE:
<223> OTHER INFORMATION: Made in Lab - cleavable peptide linker

<400> SEQUENCE: 50

Ala Ala Pro Leu
1

<210> SEQ ID NO 51
<211> LENGTH: 4
<212> TYPE: PRT
<213> ORGANISM: Artificial Sequence
<220> FEATURE:
<223> OTHER INFORMATION: Made in Lab - cleavable peptide linker

<400> SEQUENCE: 51

Ala Ala Pro Phe
1

<210> SEQ ID NO 52
<211> LENGTH: 4
<212> TYPE: PRT
<213> ORGANISM: Artificial Sequence
<220> FEATURE:
<223> OTHER INFORMATION: Made in Lab - cleavable peptide linker
```

```
<400> SEQUENCE: 52

Ala Ala Pro Ala
1

<210> SEQ ID NO 53
<211> LENGTH: 4
<212> TYPE: PRT
<213> ORGANISM: Artificial Sequence
<220> FEATURE:
<223> OTHER INFORMATION: Made in Lab - cleavable peptide linker

<400> SEQUENCE: 53

Ala Tyr Leu Val
1

<210> SEQ ID NO 54
<211> LENGTH: 6
<212> TYPE: PRT
<213> ORGANISM: Artificial Sequence
<220> FEATURE:
<223> OTHER INFORMATION: Made in Lab - cleavable peptide linker
<220> FEATURE:
<221> NAME/KEY: MOD_RES
<222> LOCATION: (3)..(3)
<223> OTHER INFORMATION: X = Any amino acid
<220> FEATURE:
<221> NAME/KEY: MOD_RES
<222> LOCATION: (6)..(6)
<223> OTHER INFORMATION: X = Any amino acid

<400> SEQUENCE: 54

Gly Pro Xaa Gly Pro Xaa
1               5

<210> SEQ ID NO 55
<211> LENGTH: 4
<212> TYPE: PRT
<213> ORGANISM: Artificial Sequence
<220> FEATURE:
<223> OTHER INFORMATION: Made in Lab - cleavable peptide linker
<220> FEATURE:
<221> NAME/KEY: MOD_RES
<222> LOCATION: (4)..(4)
<223> OTHER INFORMATION: X = Any amino acid

<400> SEQUENCE: 55

Leu Gly Pro Xaa
1

<210> SEQ ID NO 56
<211> LENGTH: 6
<212> TYPE: PRT
<213> ORGANISM: Artificial Sequence
<220> FEATURE:
<223> OTHER INFORMATION: Made in Lab - cleavable peptide linker
<220> FEATURE:
<221> NAME/KEY: MOD_RES
<222> LOCATION: (6)..(6)
<223> OTHER INFORMATION: X = Any amino acid

<400> SEQUENCE: 56

Gly Pro Ile Gly Pro Xaa
1               5

<210> SEQ ID NO 57
<211> LENGTH: 5
<212> TYPE: PRT
<213> ORGANISM: Artificial Sequence
```

```
<220> FEATURE:
<223> OTHER INFORMATION: Made in Lab - cleavable peptide linker
<220> FEATURE:
<221> NAME/KEY: MOD_RES
<222> LOCATION: (5)..(5)
<223> OTHER INFORMATION: X = Any amino acid

<400> SEQUENCE: 57

Ala Pro Gly Leu Xaa
1               5

<210> SEQ ID NO 58
<211> LENGTH: 7
<212> TYPE: PRT
<213> ORGANISM: Artificial Sequence
<220> FEATURE:
<223> OTHER INFORMATION: Made in Lab - cleavable peptide linker
<220> FEATURE:
<221> NAME/KEY: MOD_RES
<222> LOCATION: (7)..(7)
<223> OTHER INFORMATION: X = Any amino acid

<400> SEQUENCE: 58

Pro Leu Gly Pro Asp Arg Xaa
1               5

<210> SEQ ID NO 59
<211> LENGTH: 7
<212> TYPE: PRT
<213> ORGANISM: Artificial Sequence
<220> FEATURE:
<223> OTHER INFORMATION: Made in Lab - cleavable peptide linker
<220> FEATURE:
<221> NAME/KEY: MOD_RES
<222> LOCATION: (7)..(7)
<223> OTHER INFORMATION: X = Any amino acid

<400> SEQUENCE: 59

Pro Leu Gly Leu Leu Gly Xaa
1               5

<210> SEQ ID NO 60
<211> LENGTH: 7
<212> TYPE: PRT
<213> ORGANISM: Artificial Sequence
<220> FEATURE:
<223> OTHER INFORMATION: Made in Lab - cleavable peptide linker

<400> SEQUENCE: 60

Pro Gln Gly Ile Ala Gly Trp
1               5

<210> SEQ ID NO 61
<211> LENGTH: 5
<212> TYPE: PRT
<213> ORGANISM: Artificial Sequence
<220> FEATURE:
<223> OTHER INFORMATION: Made in Lab - cleavable peptide linker

<400> SEQUENCE: 61

Pro Leu Gly Cys His
1               5

<210> SEQ ID NO 62
<211> LENGTH: 6
<212> TYPE: PRT
<213> ORGANISM: Artificial Sequence
<220> FEATURE:
<223> OTHER INFORMATION: Made in Lab - cleavable peptide linker
```

```
<400> SEQUENCE: 62

Pro Leu Gly Leu Tyr Ala
1               5

<210> SEQ ID NO 63
<211> LENGTH: 7
<212> TYPE: PRT
<213> ORGANISM: Artificial Sequence
<220> FEATURE:
<223> OTHER INFORMATION: Made in Lab - cleavable peptide linker

<400> SEQUENCE: 63

Pro Leu Ala Leu Trp Ala Arg
1               5

<210> SEQ ID NO 64
<211> LENGTH: 7
<212> TYPE: PRT
<213> ORGANISM: Artificial Sequence
<220> FEATURE:
<223> OTHER INFORMATION: Made in Lab - cleavable peptide linker

<400> SEQUENCE: 64

Pro Leu Ala Tyr Trp Ala Arg
1               5

<210> SEQ ID NO 65
<211> LENGTH: 7
<212> TYPE: PRT
<213> ORGANISM: Artificial Sequence
<220> FEATURE:
<223> OTHER INFORMATION: Made in Lab - cleavable peptide linker

<400> SEQUENCE: 65

Pro Tyr Ala Tyr Tyr Met Arg
1               5

<210> SEQ ID NO 66
<211> LENGTH: 7
<212> TYPE: PRT
<213> ORGANISM: Artificial Sequence
<220> FEATURE:
<223> OTHER INFORMATION: Made in Lab - cleavable peptide linker

<400> SEQUENCE: 66

Pro Leu Gly Met Tyr Ser Arg
1               5

<210> SEQ ID NO 67
<211> LENGTH: 4
<212> TYPE: PRT
<213> ORGANISM: Artificial Sequence
<220> FEATURE:
<223> OTHER INFORMATION: Made in Lab - cleavable peptide linker

<400> SEQUENCE: 67

Gly Asp Lys Pro
1

<210> SEQ ID NO 68
<211> LENGTH: 5
<212> TYPE: PRT
<213> ORGANISM: Artificial Sequence
<220> FEATURE:
<223> OTHER INFORMATION: Made in Lab - cleavable peptide linker
```

```
<400> SEQUENCE: 68

Gly Ser Asp Lys Pro
1               5

<210> SEQ ID NO 69
<211> LENGTH: 4
<212> TYPE: PRT
<213> ORGANISM: Artificial Sequence
<220> FEATURE:
<223> OTHER INFORMATION: Made in Lab - cleavable peptide linker

<400> SEQUENCE: 69

Ala Leu Ala Leu
1

<210> SEQ ID NO 70
<211> LENGTH: 4
<212> TYPE: PRT
<213> ORGANISM: Artificial Sequence
<220> FEATURE:
<223> OTHER INFORMATION: Made in Lab - cleavable peptide linker

<400> SEQUENCE: 70

Gly Phe Leu Gly
1
```

ULINASTATIN POLYPEPTIDES

CROSS-REFERENCE TO RELATED APPLICATIONS

This application claims the benefit under 35 U.S.C. § 119(e) to U.S. Provisional Application No. 62/985,499, filed Mar. 5, 2020; U.S. Provisional Application No. 63/021,938, filed May 8, 2020; and U.S. Provisional Application No. 63/108,773, filed Nov. 2, 2020, each of which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is DIAM_039_03_US_ST25.txt. The text file is about 31 KB, was created on Mar. 5, 2021, and is being submitted electronically via EFS-Web.

BACKGROUND

Technical Field

Embodiments of the present disclosure include ulinastatin glycoforms, ulinastatin fusion polypeptides, and related compositions, mixtures, and methods of use, including methods of recombinantly producing ulinastatin polypeptides and treating diseases.

Description of the Related Art

Ulinastatin (also urinary-trypsin inhibitor) is a glycoprotein proteinase inhibitor derived from human urine which inhibits the activity of trypsin, chymotrypsin, lactate, lipase, hyaluronidase, and various pancreatic enzymes. Highly-purified ulinastatin has been used clinically for the treatment of acute pancreatitis, chronic pancreatitis, Stevens-Johnson syndrome, burns, septic shock, toxic epidermal necrolysis (TEN), and other diseases.

Ulinastatin is approved for human use for a variety of conditions, including pancreatitis. However, large quantities of ulinastatin are required because it is a serpin, a potent protease inhibitor that reacts irreversibly with the active site of the protease and is thus typically consumed in a 1:1 stoichiometry with its target. This property, coupled with the relatively low in vivo exposures achieved after systemic dosing, creates challenges in generating therapeutics from the native ulinastatin protein.

Therefore, there is a need in the art for ulinastatin polypeptides having improved characteristics related to their recombinant production and/or therapeutic utility, and related methods of producing recombinant ulinastatin polypeptides.

BRIEF SUMMARY

Embodiments of the present disclosure include an isolated, mature ulinastatin polypeptide, comprising (i) a modified O-linked glycosylation site at residues Glu-Gly-Ser-Gly (SEQ ID NO: 10) which reduces glycosylation at the O-linked glycosylation site, (ii) an N-linked glycan at residue at residue N45, and (iii) an O-linked glycan at residue T17, the residues being defined by SEQ ID NO: 2 or 4, wherein the ulinastatin polypeptide has at least one ulinastatin activity.

In some embodiments, the isolated, mature ulinastatin polypeptide comprises, consists, or consists essentially of an amino acid sequence that is at least 80, 85, 90, 95, 96, 97, 98, 99, or 100% identical to SEQ ID NO: 2 or 4, wherein the ulinastatin polypeptide comprises or retains (i) the modified O-linked glycosylation site, (ii) the N-linked glycan at residue at residue N45, and (iii) the O-linked glycan at residue T17, wherein the ulinastatin polypeptide has at least one ulinastatin activity. In some embodiments, the isolated, mature ulinastatin polypeptide comprises, consists, or consists essentially of an amino acid sequence that is at least 80, 85, 90, 95, 96, 97, 98, 99, or 100% identical to SEQ ID NO: 2, wherein the ulinastatin polypeptide comprises or retains (i) the S10A substitution of SEQ ID NO: 2, (ii) the N-linked glycan at residue at residue N45, and (iii) the O-linked glycan at residue T17, wherein the ulinastatin polypeptide has at least one ulinastatin activity. In specific embodiments, the isolated, mature ulinastatin polypeptide comprises, consists, or consists essentially of SEQ ID NO: 2, and comprises the N-linked glycan at residue at residue N45 and the O-linked glycan at residue T17.

In some embodiments, the at least one ulinastatin activity is selected from one or more of protease inhibitor activities, anti-inflammatory activities, and anti-metastatic activities. In some embodiments, the ulinastatin polypeptide has a specific activity of about or at least about 1000-3000 U/mg, or about or at least about 1000, 1100, 1200, 1300, 1400, 1500, 1600, 1700, 1800, 1900, 2000, 2100, 2200, 2300, 2400, 2500, 2600, 2700, 2800, 2900, or 3000 U/mg, wherein one unit (U) is an amount of the ulinastatin polypeptide that inhibits the activity of 2 µg trypsin by 50%.

Also included are therapeutic compositions, comprising an isolated, mature ulinastatin polypeptide described herein, and a pharmaceutically-acceptable carrier. Some compositions comprise a mixture of (a) the isolated, mature ulinastatin polypeptide described herein, and (b) a second, mature ulinastatin polypeptide that comprises an N-linked glycan at residue N45 and does not comprise an O-linked glycan at residue T17, wherein (a) and (b) have at least one ulinastatin activity. In some embodiments, the mature ulinastatin polypeptide of (b) comprises a modified O-linked glycosylation site at residues Glu-Gly-Ser-Gly (SEQ ID NO: 10) which reduces glycosylation at the O-linked glycosylation site, and has at least one ulinastatin activity. In some embodiments, the mature ulinastatin polypeptide of (b) comprises, consists, or consists essentially of an amino acid sequence that is at least 80, 85, 90, 95, 96, 97, 98, 99, or 100% identical to SEQ ID NO: 2 or 4, comprises or retains the modified O-linked glycosylation site and the N-linked glycan at residue N45, does not comprise the O-linked glycan at residue T17, and has at least one ulinastatin activity. In some embodiments, the mature ulinastatin polypeptide of (b) comprises, consists, or consists essentially of an amino acid sequence that is at least 80, 85, 90, 95, 96, 97, 98, 99, or 100% identical to SEQ ID NO: 2, comprises or retains the S10A substitution of SEQ ID NO: 2 and the N-linked glycan at residue N45, does not comprise the O-linked glycan at residue T17, and has at least one ulinastatin activity. In specific embodiments, the mature ulinastatin polypeptide of (b) comprises, consists, or consists essentially of SEQ ID NO: 2, comprises the N-linked glycan at residue N45, does not comprise the O-linked glycan at residue T17, and has at least one ulinastatin activity.

In some embodiments, the mature ulinastatin polypeptides of (a):(b) are present in the composition at a ratio ranging from about 20:1 to about 1:20, optionally about 20:1, 15:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:15, or 1:20.

Certain therapeutic compositions are substantially free of other glycosylated isoforms (glycoforms) of ulinastatin. Certain therapeutic compositions have endotoxin levels of less than about 1 EU/mg protein, host cell protein of less than about 100 ng/mg total protein, host cell DNA of less than about 10 pg/mg total protein, and/or is substantially aggregate-free Certain embodiments include ulinastatin fusion polypeptides, comprising, in an N-terminal to C-terminal orientation, a bovine alpha-lactalbumin signal peptide and a ulinastatin polypeptide, for example, wherein the ulinastatin polypeptide comprises a modified O-linked glycosylation site at residues Glu-Gly-Ser-Gly (SEQ ID NO: 10) which reduces glycosylation at the O-linked glycosylation site, and wherein the ulinastatin polypeptide has at least one ulinastatin activity.

In certain embodiments, the bovine alpha-lactalbumin signal peptide comprises, consists, or consists essentially an amino acid sequence that is at least 80, 85, 90, 95, 96, 97, 98, 99, or 100% identical to SEQ ID NO: 5. In certain embodiments, the ulinastatin polypeptide comprises, consists, or consists essentially of an amino acid sequence that is at least 80, 85, 90, 95, 96, 97, 98, 99, or 100% identical to SEQ ID NO: 1-4, wherein the ulinastatin polypeptide has at least one ulinastatin activity, and optionally wherein the ulinastatin polypeptide has or retains an S10A substitution as defined by the sequence of mature human ulinastatin.

In certain embodiments, the ulinastatin fusion polypeptide comprises, consists, or consists essentially of an amino acid sequence that is at least 80, 85, 90, 95, 96, 97, 98, 99, or 100% to SEQ ID NO: 6 or 7, wherein the ulinastatin polypeptide has at least one ulinastatin activity, and optionally wherein the ulinastatin polypeptide has or retains an S10A substitution as defined by the sequence of mature human ulinastatin. Some embodiments include a peptide linker between the bovine alpha-lactalbumin signal peptide and the ulinastatin polypeptide, optionally wherein the peptide linker is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100 amino acids in length. In certain embodiments, the peptide linker comprises a protease cleavage site.

Some ulinastatin fusion polypeptides comprise, consist, or consist essentially of the amino acid sequence set forth in SEQ ID NO: 6. Some ulinastatin fusion polypeptides comprise, consist, or consist essentially of the amino acid sequence set forth in SEQ ID NO: 7. In certain embodiments, the at least one ulinastatin activity is selected from one or more of protease inhibitor activities, anti-inflammatory activities, and anti-metastatic activities. In certain embodiments, the ulinastatin polypeptide has a specific activity of about or at least about 1000-3000 U/mg, or about or at least about 1000, 1100, 1200, 1300, 1400, 1500, 1600, 1700, 1800, 1900, 2000, 2100, 2200, 2300, 2400, 2500, 2600, 2700, 2800, 2900, or 3000 U/mg, wherein one unit (U) is an amount of the ulinastatin polypeptide that inhibits the activity of 2 µg trypsin by 50%.

Also included are polynucleotides, encoding a ulinastatin fusion polypeptide described herein. In certain embodiments, the polynucleotide comprises, consists, or consists essentially of a nucleic acid sequence that is at least 80, 85, 90, 95, 96, 97, 98, 99, or 100% to SEQ ID NO: 8 or 9.

Also included are expression vectors, comprising a polynucleotide described herein, which is operably linked to a promoter element. In certain embodiments, the expression vector is a retroviral vector that comprises, consists, or consist essentially of the following: in a 5' to 3' orientation, a 5' long terminal repeat (LTR), a packaging region, a promoter region, the polynucleotide encoding the ulinastatin fusion polypeptide, a woodchuck hepatitis virus posttranscriptional regulatory element (WPRE), and a 3' LTR.

Also included are recombinant mammalian host cells, comprising a polynucleotide or expression vector described herein. Certain recombinant mammalian host cells are selected from an HEK293 cell, and a chinese hamster ovary (CHO) cell, for instance, a GPEx CHO (GCHO) cell. In certain embodiments, the HEK293 cell constitutively expresses gag, pro, and pol proteins (optionally from murine leukemia virus (MLV)) and a separately-transfected env protein, and secretes replication incompetent retroviral particles that encode the ulinastatin fusion polypeptide. In certain embodiments, the CHO cell expresses the ulinastatin fusion polypeptide, and expresses or over-expresses a furin polypeptide, optionally an exogenous furin polypeptide.

Some embodiments include methods for recombinantly-producing a ulinastatin polypeptide, comprising (a) expressing the ulinastatin fusion polypeptide in a recombinant mammalian host cell described herein, optionally the CHO cell or GCHO; and (b) isolating the ulinastatin polypeptide from the host cell or a medium containing the host cell, thereby recombinantly-producing the ulinastatin fusion polypeptide.

Certain embodiments include cleaving the bovine alpha-lactalbumin signal peptide from the ulinastatin polypeptide, to produce a recombinant ulinastatin polypeptide that comprises, consists, or consists essentially of an amino acid sequence that is at least 80, 85, 90, 95, 96, 97, 98, 99, or 100% identical to SEQ ID NO: 1-4, wherein the ulinastatin polypeptide has at least one ulinastatin activity. In some instances, the ulinastatin polypeptide has or retains an S10A substitution as defined by the sequence of mature human ulinastatin. In some instances, the ulinastatin polypeptide is a mature ulinastatin polypeptide, as described herein.

Some embodiments include measuring at least one ulinastatin activity of the ulinastatin polypeptide under physiological conditions, optionally of temperature, salinity, and/or pH. Some embodiments include preparing a therapeutic composition that comprises the ulinastatin polypeptide, wherein the composition has a purity of at least about 80%, 85%, 90%, 95%, 98%, or 99% on a protein basis or a weight-weight basis, and wherein the composition is substantially aggregate-free and substantially endotoxin-free.

As noted above, also included are therapeutic compositions, comprising a ulinastatin polypeptide described herein, including a mature ulinastatin polypeptide described herein, mixtures thereof (for example, mixtures comprising different ulinastatin glycoforms), and therapeutic compositions prepared according to the methods described herein. Some compositions are for use in treating a disease in a subject in need thereof, for example, wherein the disease is an inflammatory disease or cancer.

Also included are methods of treating an inflammatory disease or condition in a subject in need thereof, comprising administering to the subject a therapeutic composition described herein, thereby treating the inflammatory disease or condition in the subject. In some embodiments, the inflammatory disease or condition is selected from one or more of pancreatitis (e.g., acute pancreatitis, chronic pancreatitis, endoscopic retrograde cholangiopancreatography (ERCP)-induced pancreatitis), systemic inflammation, colitis, autoimmune encephalomyelitis, Stevens-Johnson syndrome, arthritis, renal failure, burns, sepsis/septic shock including severe sepsis and related pro-inflammatory/secondary conditions (e.g., organ failure), systemic inflammatory response syndrome (SIRS), toxic epidermal necrolysis (TEN), Kawasaki disease, kidney disease (e.g., acute kidney failure, chronic kidney disease), ischemic conditions (e.g., ischemia-reperfusion injury in the liver, kidney, heart, lungs, brain), lung inflammation and inflammatory lung conditions (e.g., pulmonary infection, pneumonia, including infectious interstitial pneumonia associated with mixed connective tissue disease, pulmonary fibrosis, acute respiratory distress syndrome), liver inflammation including hepatitis, anaphylaxis, post-operative or post-surgical complications (e.g., renal function, cardiac surgery, lung surgery, cognitive dysfunction, liver transplantation), lipopolysaccharide (LPS)-induced inflammation or tissue injury (e.g., lungs, liver, brain), inflammation or dysfunction secondary to diabetes (e.g., diabetes-induced cardiac dysfunction), burn injury, heat stroke, inflammatory or neuropathic pain, acute poisoning, hyperlipidemia-associated inflammation, autoimmunity-associated inflammation, allogeneic transplant or blood transfusion-associated inflammation, neuroinflammation, and cancer-associated inflammation.

In some embodiments, administering the modified ulinastatin polypeptide reduces one or more of protease activity, endothelial activation/damage, proinflammatory cytokine and chemokine production/release (optionally, IL-1β, MIP-1α, MCP-1, and/or CXCL1), fibrinogen synthesis, neutrophil recruitment into organs, and/or organ injury in the subject.

Also included are methods of treating, ameliorating the symptoms of, or inhibiting the progression of, a cancer in a subject in need thereof, comprising administering to the subject a therapeutic composition described herein, thereby treating, ameliorating the symptoms of, or inhibiting the progression of, a cancer in a subject in need thereof. In some embodiments, the cancer is selected from one or more of melanoma (e.g., metastatic melanoma), pancreatic cancer, bone cancer, prostate cancer, small cell lung cancer, non-small cell lung cancer (NSCLC), mesothelioma, leukemia (e.g., lymphocytic leukemia, chronic myelogenous leukemia, acute myeloid leukemia, relapsed acute myeloid leukemia), lymphoma, hepatoma (hepatocellular carcinoma), sarcoma, B-cell malignancy, breast cancer, ovarian cancer, colorectal cancer, glioma, glioblastoma multiforme, meningioma, pituitary adenoma, vestibular schwannoma, primary CNS lymphoma, primitive neuroectodermal tumor (medulloblastoma), kidney cancer (e.g., renal cell carcinoma), bladder cancer, uterine cancer, esophageal cancer, brain cancer, head and neck cancers, cervical cancer, testicular cancer, thyroid cancer, and stomach cancer.

In some embodiments, the cancer is a metastatic cancer, optionally wherein administering the modified ulinastatin polypeptide reduces cancer cell invasion and/or angiogenesis. In some embodiments, the metastatic cancer is selected from one or more of:

(a) a bladder cancer which has metastasized to the bone, liver, and/or lungs;
(b) a breast cancer which has metastasized to the bone, brain, liver, and/or lungs;
(c) a colorectal cancer which has metastasized to the liver, lungs, and/or peritoneum;
(d) a kidney cancer which has metastasized to the adrenal glands, bone, brain, liver, and/or lungs;
(e) a lung cancer which has metastasized to the adrenal glands, bone, brain, liver, and/or other lung sites;
(f) a melanoma which has metastasized to the bone, brain, liver, lung, and/or skin/muscle;
(g) a ovarian cancer which has metastasized to the liver, lung, and/or peritoneum;
(h) a pancreatic cancer which has metastasized to the liver, lung, and/or peritoneum;
(i) a prostate cancer which has metastasized to the adrenal glands, bone, liver, and/or lungs;
(j) a stomach cancer which has metastasized to the liver, lung, and/or peritoneum;
(l) a thyroid cancer which has metastasized to the bone, liver, and/or lungs; and
(m) a uterine cancer which has metastasized to the bone, liver, lung, vagina, and/or peritoneum.

DETAILED DESCRIPTION

Figure 1:
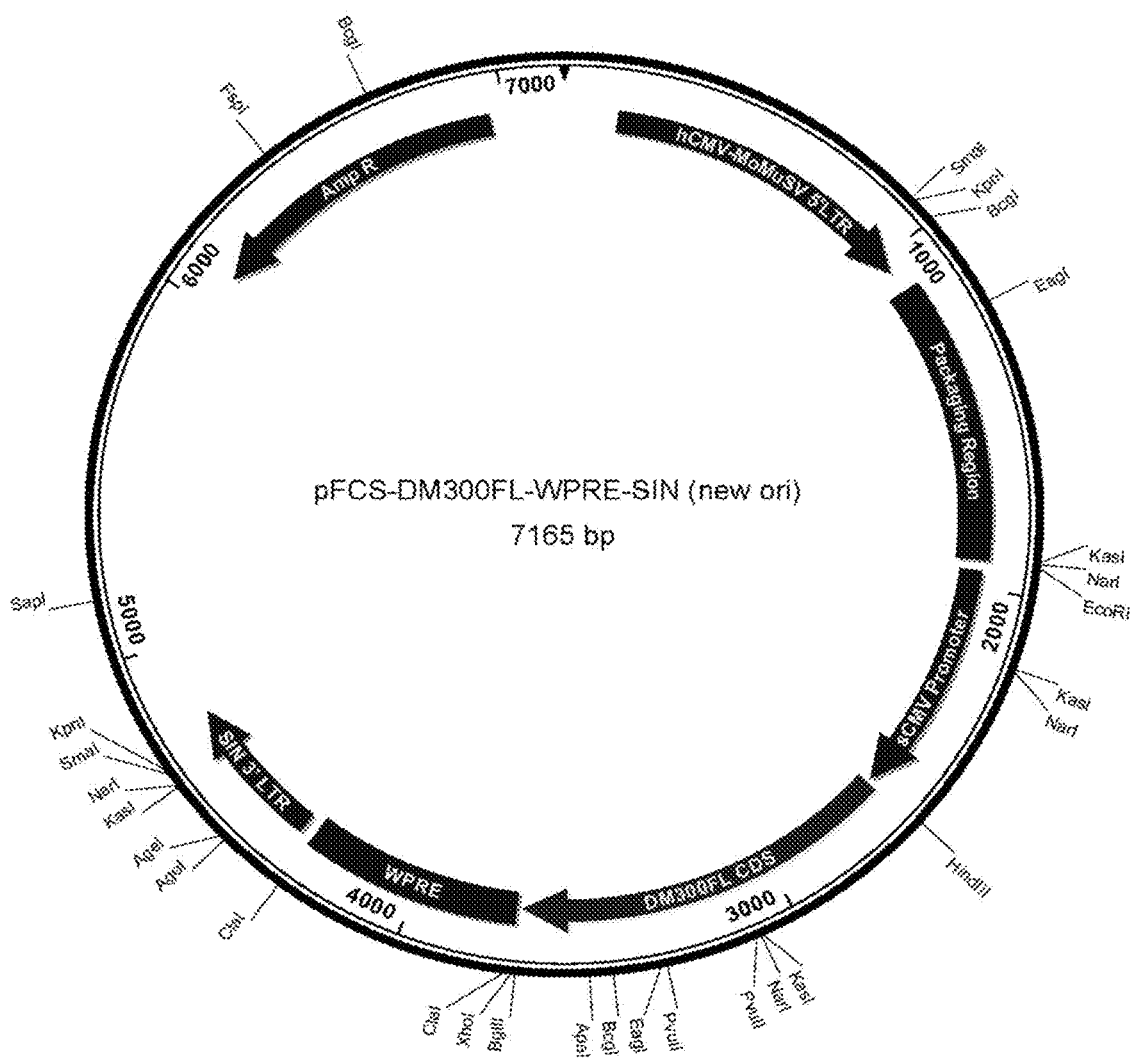
FIG. 1 shows a vector map of pFCS-DM300FL-WPRE-SIN (new ori), GDDDA01.0002, encoding the full-length ulinastatin fusion polypeptide; SEQ ID NO: 6 (polypeptide); and SEQ ID NO: 8 (nucleic acid).

Unless defined otherwise, all technical and scientific terms used herein have the same meaning as commonly understood by those of ordinary skill in the art to which the disclosure belongs. Although any methods, materials, compositions, reagents, cells, similar or equivalent similar or equivalent to those described herein can be used in the practice or testing of the subject matter of the present disclosure, preferred methods and materials are described. All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

The practice of the present disclosure will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., *Current Protocols in Protein Science*, *Current Protocols in Molecular Biology* or *Current Protocols in Immunology*, John Wiley & Sons, New York, N.Y. (2009); Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery, and treatment of patients.

For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, the term "amino acid" is intended to mean both naturally occurring and non-naturally-occurring amino acids as well as amino acid analogs and mimetics. Naturally-occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

"Biocompatible" refers to materials or compounds which are generally not injurious to biological functions and which will not result in any degree of unacceptable toxicity, including allergenic and disease states.

By "coding sequence" is meant any nucleic acid sequence that contributes to the code for the polypeptide product of a gene. By contrast, the term "non-coding sequence" refers to any nucleic acid sequence that does not directly contribute to the code for the polypeptide product of a gene.

Throughout this disclosure, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "endotoxin free" or "substantially endotoxin free" relates generally to compositions, solvents, and/or vessels that contain at most trace amounts (e.g., amounts having no clinically adverse physiological effects to a subject) of endotoxin, and preferably undetectable amounts of endotoxin. Endotoxins are toxins associated with certain micro-organisms, such as bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art.

Endotoxins can be detected using routine techniques known in the art. For example, the Limulus Amoebocyte Lysate assay, which utilizes blood from the horseshoe crab, is a very sensitive assay for detecting presence of endotoxin. In this test, very low levels of LPS can cause detectable coagulation of the limulus lysate due a powerful enzymatic cascade that amplifies this reaction. Endotoxins can also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/mg of active compound. Typically, 1 ng lipopolysaccharide (LPS) corresponds to about 1-10 EU.

The "half-life" of a polypeptide can refer to the time it takes for the polypeptide to lose half of its pharmacologic, physiologic, or other activity, relative to such activity at the time of administration into the serum or tissue of an organism, or relative to any other defined time-point. "Half-life" can also refer to the time it takes for the amount or concentration of a polypeptide to be reduced by half of a starting amount administered into the serum or tissue of an organism, relative to such amount or concentration at the time of administration into the serum or tissue of an organism, or relative to any other defined time-point. The half-life can be measured in serum and/or any one or more selected tissues.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and ranges in between e.g., 1.5, 1.6, 1.7. 1.8, etc.) the amount produced by no composition (e.g., the absence of agent) or a control composition. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and ranges in between) in the amount produced by no composition (e.g., the absence of an agent) or a control composition. Examples of comparisons and "statistically significant" amounts are described herein.

The terms "polypeptide," "protein" and "peptide" are used interchangeably and mean a polymer of amino acids not limited to any particular length. The term "enzyme" includes polypeptide or protein catalysts, and with respect to ulinastatin is used interchangeably with protein, polypeptide, or peptide. The terms include modifications such as myristoylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the ulinastatin proteins described herein, or sequences that have deletions from, additions to, and/or substitutions of one or more amino acid of the ulinastatin proteins. In certain embodiments, the polypeptide is a "recombinant" polypeptide, which is produced by recombinant cell that comprises one or more recombinant DNA molecules, which are typically made of heterologous polynucleotide sequences or combinations of polynucleotide sequences that would not otherwise be found in the cell.

The term "isolated" polypeptide or protein referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or non-covalent interaction) with portions of a protein with which the "isolated protein" is associated in nature, (6) is operably associated (by covalent or non-covalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

In certain embodiments, the "purity" of any given agent (e.g., ulinastatin polypeptide) in a composition may be specifically defined. For instance, certain compositions may comprise an agent that is at least 70, 75 80, 85, 90, 91, 92, 93, 94, 95, 96, 97, 98, 99, or 100% pure (for example, on a protein basis), including all decimals and ranges in between, as measured, for example, by high performance liquid chromatography (HPLC), a well-known form of column chromatography used frequently in biochemistry and analytical chemistry to separate, identify, and quantify compounds.

The term "reference sequence" refers generally to a nucleic acid coding sequence, or amino acid sequence, to which another sequence is being compared. All polypeptide and polynucleotide sequences described herein are included as references sequences, including those described by name and those described in the Tables and the Sequence Listing.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

The term "solubility" refers to the property of an agent (e.g., ulinastatin polypeptide) provided herein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, pH 7.4, pH 7.6, pH 7.8, or pH 8.0 (e.g., about pH 5-8). In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (37° C.). In certain embodiments, an agent has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90 or 100 mg/ml at room temperature or at 37° C.

A "subject" or a "subject in need thereof" or a "patient" or a "patient in need thereof" includes a mammalian subject such as a human subject.

"Substantially" or "essentially" means nearly totally or completely, for instance, 95%, 96%, 97%, 98%, 99% or greater of some given quantity.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

"Therapeutic response" refers to improvement of symptoms (whether or not sustained) based on administration of one or more therapeutic agents.

As used herein, "treatment" of a subject (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

The term "wild-type" refers to a gene or gene product (e.g., a polypeptide) that is most frequently observed in a population and is thus arbitrarily designed the "normal" or "wild-type" form of the gene.

Each embodiment in this specification is to be applied mutatis mutandis to every other embodiment unless expressly stated otherwise.

Ulinastatin Glycoforms and Fusion Polypeptides

Certain embodiments of the present disclosure relate generally to alternate glycoforms of human ulinastatin, including a mature human ulinastatin polypeptide having an unexpected O-linked glycan at residue threonine 17 (T17), including active or functional variants and fragments thereof. Some embodiments relate to "ulinastatin fusion polypeptides", comprising a "bovine alpha-lactalbumin signal peptide" and a "ulinastatin polypeptide", including active or otherwise functional variants and fragments thereof.

"Ulinastatin" (also referred to as urinary trypsin inhibitor (UTI), HI-30, ASPI, or bikunin) is an acidic glycoprotein with a molecular weight of about 30 kDa by SDS-polyacrylamide gel electrophoresis. Wild-type, mature human ulinastatin is a multivalent Kunitz-type serine protease inhibitor found in human urine and blood that is composed of 147 amino acid residues includes two Kunitz-type domains (see Table U1). It is produced by hepatocytes as a full-length precursor (see Table U1) in which ulinastatin is linked to α1-microglobulin. In hepatocytes, different types of ulinastatin-containing proteins are formed by the assembly of ulinastatin, with one or two of the three evolutionarily related heavy chains (HC) 1, HC 2, and HC 3, through a chondroitin sulfate chain; these proteins comprise inter-α-inhibitor (IαI) family members, including IαI, pre-α-inhibitor (PαI), inter-α-like inhibitor (IαLI), and free ulinastatin. IαI, pαI, and IαLI are composed of HC1+HC2+UTI, HC3+UTI, and HC2+UTI, respectively.

During inflammation, ulinastatin is cleaved from IαI family proteins through proteolytic cleavage by neutrophil elastase in the peripheral circulation or at the inflammatory site, and plasma ulinastatin levels and gene expression are altered in severe inflammatory conditions. Thus, plasma ulinastatin is considered to be one of the acute phase reactions. Further, ulinastatin is rapidly released into urine when infection occurs and is an excellent inflammatory marker, constituting most of the urinary anti-trypsin activity. Various serine proteases such as trypsin, chymotrypsin, kallikrein, plasmin, granulocyte elastase, cathepsin, thrombin, and Factors IXa, Xa, XIa, and XIIa are inhibited by ulinastatin. Furthermore, ulinastatin can suppress urokinase-type plasminogen activator (uPA) expression through the inhibition of protein kinase C (PKC). Ulinastatin appears to prevent organ injury by inhibiting the activity of these proteases.

Beyond its inhibition of inflammatory proteases mentioned above, ulinastatin exhibits anti-inflammatory activity and suppresses the infiltration of neutrophils and release of elastase and chemical mediators from them. Likewise, ulinastatin inhibits the production of tumor necrosis factor (TNF)-α and interleukin (IL)-1 in LPS-stimulated human monocytes and LPS- or neutrophil elastase-stimulated IL-8 gene expression in HL60 cells or bronchial epithelial cells in vitro. It has also been shown to inhibit LPS-induced TNF-α and subsequent IL-1β and IL-6 induction by macrophages, at least partly, through the suppression of mitogen-activated protein kinase (MAPK) signaling pathways such as ERK1/2, JNK, and p38 in vitro. Ulinastatin also inhibits neutrophil-mediated endothelial cell injury in vitro, suggesting that it can act directly/indirectly on neutrophils and suppress their production and secretion of activated elastase. Furthermore, ulinastatin down-regulates stimulated arachidonic acid metabolism such as thromboxane B2 production in vitro, which plays a role in the pathogenesis of sepsis.

In particular embodiments, the ulinastatin polypeptide is a human ulinastatin polypeptide, or a variant or fragment thereof. The amino acid sequences of exemplary human ulinastatin polypeptides are provided in Table U1 below.

(SEQ ID NO: 10) O-linked glycosylation site. The CS chain is relatively short (Mwt~8000) with 12-18 disaccharide repeats (GlcUA 1,3-GalNac1,4-) and a conventional linkage region (GlcUA 1-3Gal 1-3Gal 1-4Xyl 1)-O-Ser. About 30% of the GalNAc, usually those near the linkage region, are sulfated at C-4 hydroxyl groups. CS chains synthesized during inflammations are shorter with decreased sulfation. Thus, in some instances, a ulinastatin polypeptide comprises at least one substitution and/or deletion at one or more of the Glu-Gly-Ser-Gly (SEQ ID NO: 10) residues of mature ulinastatin, which reduces glycosylation at the O-linked glycosylation site. In specific embodiments, a ulinastatin polypeptide comprises a substitution or deletion at position S10, for example, an S10A substitution, as defined by the mature ulinastatin sequence. Also, in certain embodiments, a ulinastatin polypeptide has a naturally-occurring N-linked glycan at residue asparagine 45 (N45).

Certain embodiments thus include an isolated, mature ulinastatin polypeptide, comprising (i) a modified O-linked glycosylation site at residues Glu-Gly-Ser-Gly (SEQ ID NO: 10) which reduces glycosylation at the O-linked glycosylation site, (ii) an N-linked glycan at residue at residue N45, and (iii) an O-linked glycan at residue T17, the residues being defined by SEQ ID NO: 2 or 4, wherein the ulinastatin polypeptide has at least one ulinastatin activity. In some embodiments, a mature ulinastatin polypeptide comprises,

TABLE U1

Exemplary Ulinastatin Sequences

| Description | Sequence | SEQ ID NO: |
|---|---|---|
| FL Human Ulinastatin S10A Mutation | GPVPAPPDNIQVQENFNISRIYGKWYNLAIGSTCPWLKKIMDRMTVSTLVLG EGATEAEISMTSTRWRKGVCEETSGAYEKTDTDGKFLYHKSKWNITMESYVV HTNYDEYAIFLTKKFSRHHGPTITAKLYGRAPQLRETLLQDFRVVAQGVGIP EDSIFTMADRGECVPGEQEPEPILIPRVRRAVLPQEEEGAGGGQLVTEVTKK EDSCQLGYSAGPCMGMTSRYFYNGTSMACETFQYGGCMGNGNNFVTEKECLQ TCRTVAACNLPIVRGPCRAFIQLWAFDAVKGKCVLFPYGGCQGNGNKFYSEK ECREYCGVPGDGDEELLRFSN | 1 |
| Mature Human Ulinastatin S10A Mutation | AVLPQEEEGAGGGQLVTEVTKKEDSCQLGYSAGPCMGMTSRYFYNGTSMACE TFQYGGCMGNGNNFVTEKECLQTCRTVAACNLPIVRGPCRAFIQLWAFDAVK GKCVLFPYGGCQGNGNKFYSEKECREYCGVPGDGDEELLRFSN | 2 |
| FL WT Human Ulinastatin | GPVPAPPDNIQVQENFNISRIYGKWYNLAIGSTCPWLKKIMDRMTVSTLVLG EGATEAEISMTSTRWRKGVCEETSGAYEKTDTDGKFLYHKSKWNITMESYVV HTNYDEYAIFLTKKFSRHHGPTITAKLYGRAPQLRETLLQDFRVVAQGVGIP EDSIFTMADRGECVPGEQEPEPILIPRVRRAVLPQEEEGSGGGQLVTEVTKK EDSCQLGYSAGPCMGMTSRYFYNGTSMACETFQYGGCMGNGNNFVTEKECLQ TCRTVAACNLPIVRGPCRAFIQLWAFDAVKGKCVLFPYGGCQGNGNKFYSEK ECREYCGVPGDGDEELLRFSN | 3 |
| WT Mature Human Ulinastatin | AVLPQEEEGSGGGQLVTEVTKKEDSCQLGYSAGPCMGMTSRYFYNGTSMACE TFQYGGCMGNGNNFVTEKECLQTCRTVAACNLPIVRGPCRAFIQLWAFDAVK GKCVLFPYGGCQGNGNKFYSEKECREYCGVPGDGDEELLRFSN | 4 |

Thus, in some embodiments, a mature ulinastatin polypeptide, comprises, consists, or consists essentially of an amino acid sequence that is least 80, 85, 90, 95, 96, 97, 98, or 99% identical to SEQ ID NO: 2 or 4, and has or retains an O-linked glycan at residue T17 as defined by SEQ ID NO: 2 or 4, wherein the ulinastatin polypeptide has at least one ulinastatin activity. Also, in certain embodiments, the ulinastatin polypeptide portion of a ulinastatin fusion polypeptide comprises, consists, or consists essentially of an amino acid sequence that is least 80, 85, 90, 95, 96, 97, 98, or 99% identical to a sequence selected from Table U1 (SEQs: 1-4).

Certain ulinastatin polypeptides have a modified O-linked glycosylation site. Here, serine 10 has a chondroitin sulfate (CS) chain attached at a well-conserved Glu-Gly-Ser-Gly consists, or consists essentially of an amino acid sequence that is at least 80, 85, 90, 95, 96, 97, 98, 99, or 100% identical to SEQ ID NO: 2 or 4, wherein the ulinastatin polypeptide comprises or retains (i) the modified O-linked glycosylation site, (ii) the N-linked glycan at residue at residue N45, and (iii) the O-linked glycan at residue T17, wherein the ulinastatin polypeptide has at least one ulinastatin activity. Specific examples of mature ulinastatin polypeptides comprise, consist, or consist essentially of an amino acid sequence that is at least 80, 85, 90, 95, 96, 97, 98, 99, or 100% identical to SEQ ID NO: 2, wherein the ulinastatin polypeptide comprises or retains (i) the S10A substitution of SEQ ID NO: 2, (ii) the N-linked glycan at residue at residue N45, and (iii) the O-linked glycan at residue T17, wherein the ulinastatin polypeptide has at least one ulinastatin activity.

In some embodiments, a ulinastatin polypeptide has at least one "ulinastatin activity". The term "ulinastatin activity" includes (a) protease inhibitor activities, which include reducing the protease activity of one or more of trypsin, chymotrypsin, kallikrein, plasmin, granulocyte elastase, cathepsin, thrombin, and/or factors IXa, Xa, XIa, and XIIa; (b) anti-inflammatory activities, which include reducing inflammation and/or cytokine-depending signaling pathways, for instance, to reduce organ injury during severe inflammation; and (c) anti-metastatic activities, which include reducing tumor invasion and metastasis, for example, by reducing cathepsin B activity and/or reducing CD44 dimerization, at least the latter of which suppresses the MAP kinase signaling cascade and reduces extracellular matrix (ECM) degradation, tumor cell invasion, and/or angiogenesis.

In certain embodiments, a ulinastatin polypeptide has a "specific activity" of about or at least about 500-5000 U/mg, or about or at least about 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000 U/mg polypeptide, wherein one unit (U) is an amount of the ulinastatin polypeptide that inhibits the activity of 2 μg trypsin by 50%.

As noted above, the ulinastatin fusion polypeptides described herein comprise a bovine alpha-lactalbumin signal peptide, or a variant or fragment thereof. The sequence of an exemplary signal peptide is provided in Table S1 below.

TABLE S1

Exemplary Signal Peptide Sequence(s)

| Description | Sequence | SEQ ID NO: |
|---|---|---|
| Bovine alpha-lactalbumin signal peptide | MMSFVSLLLVGILFHATQA | 5 |

Thus, in certain embodiments, the bovine alpha-lactalbumin signal peptide portion of the ulinastatin fusion polypeptide comprises, consists, or consists essentially of an amino acid sequence that is at least 80, 85, 90, 95, 96, 97, 98, 99, or 100% identical to SEQ ID NO: 5.

The amino acid sequences of exemplary ulinastatin fusion polypeptides are provided in Table U2 below.

TABLE U2

Exemplary Ulinastatin Fusion Polypeptides

| Description | Sequence | SEQ ID NO: |
|---|---|---|
| FL Human Ulinastatin S10A Mutation with Signal Sequence (underlined) | MMSFVSLLLVGILFHATQAGPVPAPPDNIQVQENFNISRIYGKWYNLAI GSTCPWLKKIMDRMTVSTLVLGEGATEAEISMTSTRWRKGVCEETSGAY EKTDTDGKFLYHKSKWNITMESYVVHTNYDEYAIFLTKKFSRHHGPTIT AKLYGRAPQLRETLLQDFRVVAQGVGIPEDSIFTMADRGECVPGEQEPE PILIPRVRRAVLPQEEEGAGGGQLVTEVTKKEDSCQLGYSAGPCMGMTS RYFYNGTSMACETFQYGGCMGNGNNFVTEKECLQTCRTVAACNLPIVRG PCRAFIQLWAFDAVKGKCVLFPYGGCQGNGNKFYSEKECREYCGVPGDG DEELLRFSN | 6 |
| Mature Human Ulinastatin S10A Mutation with Signal Sequence (underlined) | MMSFVSLLLVGILFHATQAAVLPQEEEGAGGGQLVTEVTKKEDSCQLGY SAGPCMGMTSRYFYNGTSMACETFQYGGCMGNGNNFVTEKECLQTCRTV AACNLPIVRGPCRAFIQLWAFDAVKGKCVLFPYGGCQGNGNKFYSEKEC REYCGVPGDGDEELLRFSN | 7 |

Thus, in some embodiments, a ulinastatin fusion polypeptide, or a variant or fragment thereof, comprises, consists, or consists essentially of an amino acid sequence that is at least 80, 85, 90, 95, 96, 97, 98, 99, or 100% identical to a sequence selected from Table U2, and which has at least one ulinastatin activity. In certain embodiments, the ulinanastatin portion of the fusion polypeptide from Table U2 comprises or retains a modified O-linked glycosylation site at residues Glu-Gly-Ser-Gly (SEQ ID NO: 10) which reduces glycosylation at the O-linked glycosylation site, such as substitution or deletion at position S10, for example, an S10A substitution A "variant" sequence refers to a polypeptide or polynucleotide sequence that differs from a reference sequence by one or more substitutions, deletions (e.g., truncations), additions, and/or insertions. Certain variants thus include fragments of a reference sequence described herein. Variant polypeptides are biologically active, that is, they continue to possess the enzymatic or binding activity of a reference polypeptide. Such variants may result from, for example, genetic polymorphism and/or from human manipulation.

In some instances, a variant comprises one or more "conservative" changes or substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present disclosure and still obtain a functional molecule that encodes a variant or derivative polypeptide with desirable characteristics. When it is desired to alter the amino acid sequence of a polypeptide to create an equivalent, or even an improved, variant or portion of a polypeptide described herein, one skilled in the art will typically change one or more of the codons of the encoding DNA sequence.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their utility.

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte & Doolittle, 1982). These values are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A variant may also, or alternatively, contain non-conservative changes. In some embodiments, variant polypeptides differ from a native or reference sequence by substitution, deletion or addition of about or fewer than about 10, 9, 8, 7, 6, 5, 4, 3, 2 amino acids, or even 1 amino acid. Variants may also (or alternatively) be modified by, for example, the deletion or addition of amino acids that have minimal influence on the immunogenicity, secondary structure, enzymatic activity, and/or hydropathic nature of the polypeptide.

In certain embodiments, a polypeptide sequence is about, at least about, or up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, or 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 800, 810, 820, 830, 840, 850, 860, 870, 880, 890, 900, 900, 910, 920, 930, 940, 950, 960, 970, 980, 990, 1000 or more contiguous amino acids in length, including all integers in between, and which may comprise all or a portion of a reference sequence (see, e.g., Table U1, Table S1, Table U2, Sequence Listing).

In some embodiments, a polypeptide sequence consists of about or no more than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 800, 810, 820, 830, 840, 850, 860, 870, 880, 890, 900, 900, 910, 920, 930, 940, 950, 960, 970, 980, 990, 1000 or more contiguous amino acids, including all integers in between, and which may comprise all or a portion of a reference sequence (see, e.g., Table U1, Table S1, Table U2, Sequence Listing).

In certain embodiments, a polypeptide sequence is about 10-1000, 10-900, 10-800, 10-700, 10-600, 10-500, 10-400, 10-300, 10-200, 10-100, 10-50, 10-40, 10-30, 10-20, 20-1000, 20-900, 20-800, 20-700, 20-600, 20-500, 20-400, 20-300, 20-200, 20-100, 20-50, 20-40, 20-30, 50-1000, 50-900, 50-800, 50-700, 50-600, 50-500, 50-400, 50-300, 50-200, 50-100, 100-1000, 100-900, 100-800, 100-700, 100-600, 100-500, 100-400, 100-300, 100-200, 200-1000, 200-900, 200-800, 200-700, 200-600, 200-500, 200-400, or 200-300 contiguous amino acids, including all ranges in between, and comprises all or a portion of a reference sequence (see, e.g., Table U1, Table S1, Table U2 Sequence Listing). In certain embodiments, the C-terminal or N-terminal region of any reference polypeptide may be truncated by about 1, 2, 3, 4, 5, 6, 7, 8, 9, 10, 15, 20, 25, 30, 35, 40, 45, 50, 60, 70, 80, 90, or 100 or more amino acids, or by about 10-50, 20-50, 50-100 or more amino acids, including all integers and ranges in between (e.g., 101, 102, 103, 104, 105), so long as the truncated polypeptide retains the binding properties and/or activity of the reference polypeptide (see, e.g., Table U1, Table S1, Table U2, Sequence Listing). Typically, the biologically-active fragment has no less than about 1%, about 5%, about 10%, about 25%, about 50%, about 60%, about 70%, about 80%, about 90%, or about 100% of an activity of the biologically-active reference polypeptide from which it is derived.

In general, variants will display at least about 30%, 40%, 50%, 55%, 60%, 65%, 70%, 75%, 80%, 85%, 90%, 91%, 92%, 93%, 94%, 95%, 96%, 97%, 98%, 99% similarity or sequence identity or sequence homology to a reference polypeptide sequence (see, e.g., Table U1, Table U2, Sequence Listing). Moreover, sequences differing from the native or parent sequences by the addition (e.g., C-terminal addition, N-terminal addition, both), deletion, truncation, insertion, or substitution (e.g., conservative substitution) of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 amino acids (including all integers and ranges in between) but which retain the properties or activities of a parent or reference polypeptide sequence are contemplated (see, e.g., Table U1, Table S1, Table U2, Sequence Listing).

In some embodiments, variant polypeptides differ from reference sequence by at least one but by less than 50, 40, 30, 20, 15, 10, 8, 6, 5, 4, 3 or 2 amino acid residue(s). In certain embodiments, variant polypeptides differ from a reference sequence by at least 1% but less than 20%, 15%, 10% or 5% of the residues. (If this comparison requires alignment, the sequences should be aligned for maximum similarity. "Looped" out sequences from deletions or insertions, or mismatches, are considered differences.)

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (*J. Mol. Biol.* 48: 444-453, 1970) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (*Cabios.* 4:11-17, 1989) which has been incorporated into the ALIGN program (version 2.0), using a PAM120 weight residue table, a gap length penalty of 12 and a gap penalty of 4.

The sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to nucleic acid molecules described herein. BLAST protein searches can be performed with the XBLAST program, score=50, wordlength=3 to obtain amino acid sequences homologous to protein molecules described herein. To obtain gapped alignments for comparison purposes, Gapped BLAST can be utilized as described in Altschul et al., (*Nucleic Acids Res.* 25: 3389-3402, 1997). When utilizing BLAST and Gapped BLAST programs, the default parameters of the respective programs (e.g., XBLAST and NBLAST) can be used.

In some embodiments, as noted above, polynucleotides and/or polypeptides can be evaluated using a BLAST alignment tool. A local alignment consists simply of a pair of sequence segments, one from each of the sequences being compared. A modification of Smith-Waterman or Sellers algorithms will find all segment pairs whose scores cannot be improved by extension or trimming, called high-scoring segment pairs (HSPs). The results of the BLAST alignments include statistical measures to indicate the likelihood that the BLAST score can be expected from chance alone.

The raw score, S, is calculated from the number of gaps and substitutions associated with each aligned sequence wherein higher similarity scores indicate a more significant alignment. Substitution scores are given by a look-up table (see PAM, BLOSUM).

Gap scores are typically calculated as the sum of G, the gap opening penalty and L, the gap extension penalty. For a gap of length n, the gap cost would be G+Ln. The choice of gap costs, G and L is empirical, but it is customary to choose a high value for G (10-15), e.g., 11, and a low value for L (1-2) e.g., 1.

The bit score, S', is derived from the raw alignment score S in which the statistical properties of the scoring system used have been taken into account. Bit scores are normalized with respect to the scoring system, therefore they can be used to compare alignment scores from different searches. The terms "bit score" and "similarity score" are used interchangeably. The bit score gives an indication of how good the alignment is; the higher the score, the better the alignment.

The E-Value, or expected value, describes the likelihood that a sequence with a similar score will occur in the database by chance. It is a prediction of the number of different alignments with scores equivalent to or better than S that are expected to occur in a database search by chance. The smaller the E-Value, the more significant the alignment. For example, an alignment having an E value of $e^{-117}$ means that a sequence with a similar score is very unlikely to occur simply by chance. Additionally, the expected score for aligning a random pair of amino acids is required to be negative, otherwise long alignments would tend to have high score independently of whether the segments aligned were related. Additionally, the BLAST algorithm uses an appropriate substitution matrix, nucleotide or amino acid and for gapped alignments uses gap creation and extension penalties. For example, BLAST alignment and comparison of polypeptide sequences are typically done using the BLOSUM62 matrix, a gap existence penalty of 11 and a gap extension penalty of 1.

In some embodiments, sequence similarity scores are reported from BLAST analyses done using the BLOSUM62 matrix, a gap existence penalty of 11 and a gap extension penalty of 1.

In a particular embodiment, sequence identity/similarity scores provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff, *PNAS USA.* 89:10915-10919, 1992). GAP uses the algorithm of Needleman and Wunsch (*J Mol Biol.* 48:443-453, 1970) to find the alignment of two complete sequences that maximizes the number of matches and minimizes the number of gaps.

In particular embodiments, the variant polypeptide comprises an amino acid sequence that can be optimally aligned with a reference polypeptide sequence (see, e.g., Table U1, Table U2, Sequence Listing) to generate a BLAST bit scores or sequence similarity scores of at least about 50, 60, 70, 80, 90, 100, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or more, including all integers and ranges in between, wherein the BLAST alignment used the BLOSUM62 matrix, a gap existence penalty of 11, and a gap extension penalty of 1.

As noted above, a reference polypeptide may be altered in various ways including amino acid substitutions, deletions, truncations, additions, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (*PNAS USA.* 82: 488-492, 1985); Kunkel et al., (*Methods in Enzymol.* 154: 367-382, 1987), U.S. Pat. No. 4,873,192, Watson, J. D. et al., ("Molecular Biology of the Gene," Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Methods for screening gene products of combinatorial libraries made by such modifications, and for screening cDNA libraries for gene products having a selected property are known in the art. Such methods are adaptable for rapid screening of the gene libraries generated by combinatorial mutagenesis of reference polypeptides. As one example, recursive ensemble mutagenesis (REM), a technique which enhances the frequency of functional mutants in the libraries, can be used in combination with the screening assays to identify polypeptide variants (Arkin and Yourvan, *PNAS USA* 89: 7811-7815, 1992; Delgrave et al., *Protein Engineering.* 6: 327-331, 1993).

In certain embodiments, a peptide linker sequence may be employed to separate the bovine alpha-lactalbumin signal peptide(s) and the ulinastatin polypeptide(s) by a distance sufficient to ensure that each polypeptide folds into its desired secondary and tertiary structures, and/or to facilitate cleavage of the signal peptide from the ulinastatin polypeptide, if desired. Such a peptide linker sequence can be incorporated into a fusion polypeptide using standard techniques well known in the art.

Certain peptide linker sequences may be chosen based on the following exemplary factors: (1) their ability to adopt a flexible extended conformation; (2) their inability to adopt a secondary structure that could interact with functional epitopes on the first and second polypeptides; (3) their physiological stability; and (4) the lack of hydrophobic or charged residues that might react with the polypeptide functional epitopes, or other features. See, e.g., George and Heringa, J Protein Eng. 15:871-879, 2002.

The linker sequence may generally be from 1 to about 200 amino acids in length. Particular linkers can have an overall amino acid length of about 1-200 amino acids, 1-150 amino acids, 1-100 amino acids, 1-90 amino acids, 1-80 amino acids, 1-70 amino acids, 1-60 amino acids, 1-50 amino acids, 1-40 amino acids, 1-30 amino acids, 1-20 amino acids, 1-10 amino acids, 1-5 amino acids, 1-4 amino acids, 1-3 amino acids, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100 or more amino acids.

A peptide linker may employ any one or more naturally-occurring amino acids, non-naturally occurring amino acid(s), amino acid analogs, and/or amino acid mimetics as described elsewhere herein and known in the art. Certain amino acid sequences which may be usefully employed as linkers include those disclosed in Maratea et al., Gene 40:39-46, 1985; Murphy et al., PNAS USA. 83:8258-8262, 1986; U.S. Pat. Nos. 4,935,233 and 4,751,180. Particular peptide linker sequences contain Gly, Ser, and/or Asn residues. Other near neutral amino acids, such as Thr and Ala may also be employed in the peptide linker sequence, if desired.

Certain exemplary linkers include Gly, Ser and/or Asn-containing linkers, as follows: $[G]_x$, $[S]_x$, $[N]_x$, $[GS]_x$, $[GGS]_x$, $[GSS]_x$, $[GSGS]_x$ (SEQ ID NO: 11), $[GGSG]_x$ (SEQ ID NO: 10), $[GGGS]_x$ (SEQ ID NO: 12), $[GGGGS]_x$ (SEQ ID NO: 13), $[GN]_x$, $[GGN]_x$, $[GNN]_x$, $[GNGN]_x$ (SEQ ID NO: 14), $[GGNG]_x$ (SEQ ID NO: 15), $[GGGN]_x$ (SEQ ID NO: 16), $[GGGGN]_x$ (SEQ ID NO: 17) linkers, where $x$ is 1, 2, 3, 4, 5, 6, 7, 8, 9, 10, 11, 12, 13, 14, 15, 16, 17, 18, 19, or 20 or more. Other combinations of these and related amino acids will be apparent to persons skilled in the art.

Additional examples of linker peptides include, but are not limited to the following amino acid sequences: Gly-Gly-Gly-Gly-Ser-Gly-Gly-Gly-Gly-Ser-Gly-Gly-Gly-Gly-Ser-(SEQ ID NO: 18); Gly-Ser-Gly-Gly-Gly-Gly-Ser-Gly-Gly-Gly-Gly-Ser-Gly-Gly-Gly-Gly-Ser-Gly-Gly-Gly-Gly-Ser-(SEQ ID NO: 19); Gly-Gly-Gly-Gly-Ser-Gly-Gly-Gly-Gly-Ser-Gly-Gly-Gly-Ser-Gly-Gly-Gly-Gly-Ser-Gly-Gly-Gly-Gly-Ser-Gly-Gly-Gly-Gly-Ser-(SEQ ID NO: 20); Asp-Ala-Ala-Ala-Lys-Glu-Ala-Ala-Ala-Lys-Asp-Ala-Ala-Ala-Arg-Glu-Ala-Ala-Ala-Arg-Asp-Ala-Ala-Ala-Lys-(SEQ ID NO: 21); and Asn-Val-Asp-His-Lys-Pro-Ser-Asn-Thr-Lys-Val-Asp-Lys-Arg-(SEQ ID NO: 22).

Further non-limiting examples of linker peptides include DGGGS (SEQ ID NO: 23); TGEKP (SEQ ID NO: 24) (see, e.g., Liu et al., PNAS. 94:5525-5530, 1997); GGRR (SEQ ID NO: 25) (Pomerantz et al. 1995); $(GGGGS)_n$ (SEQ ID NO: 13) (Kim et al., PNAS. 93:1156-1160, 1996); EGKSSGSGSESKVD (SEQ ID NO: 26) (Chaudhary et al., PNAS. 87:1066-1070, 1990); KESGSVSSEQLAQFRSLD (SEQ ID NO: 27) (Bird et al., Science. 242:423-426, 1988), GGRRGGGS (SEQ ID NO: 28); LRQRDGERP (SEQ ID NO: 29); LRQKDGGGSERP (SEQ ID NO: 30); LRQKd $(GGGS)_2$ ERP (SEQ ID NO: 31). In specific embodiments, the linker sequence comprises a Gly3 linker sequence, which includes three glycine residues. In particular embodiments, flexible linkers can be rationally designed using a computer program capable of modeling both DNA-binding sites and the peptides themselves (Desjarlais & Berg, PNAS. 90:2256-2260, 1993; and PNAS. 91:11099-11103, 1994) or by phage display methods.

In particular embodiments, the linker peptide comprises an autocatalytic or self-cleaving peptide cleavage site. In a particular embodiment, self-cleaving peptides include those polypeptide sequences obtained from potyvirus and cardiovirus 2A peptides, FMDV (foot-and-mouth disease virus), equine rhinitis A virus, Thosea asigna virus and porcine teschovirus. In certain embodiments, the self-cleaving polypeptide site comprises a 2A or 2A-like site, sequence or domain (Donnelly et al., J. Gen. Virol. 82:1027-1041, 2001). Exemplary 2A sites include the following sequences: LLNFDLLKLAGDVESNPGP (SEQ ID NO: 32); TLNFDLLKLAGDVESNPGP (SEQ ID NO: 33); LLKLAGDVESNPGP (SEQ ID NO: 34); NFDLLKLAGDVESNPGP (SEQ ID NO: 35); QLLNFDLLKLAGDVESNPGP (SEQ ID NO: 36); APVKQTLNFDLLKLAGDVESNPGP (SEQ ID NO: 37); VTELLYRMKRAETYCPRPLLAIHPTEARHKQKIVAPVKQT (SEQ ID NO: 38); LNFDLLKLAGDVESNPGP (SEQ ID NO: 39); LLAIHPTEARHKQKIVAPVKQTLNFDLLKLAGDVESNPGP (SEQ ID NO: 40); and EARHKQKIVAPVKQTLNFDLLKLAGDVESNPGP (SEQ ID NO: 41). In some embodiments, the autocatalytic peptide cleavage site comprises a translational 2A signal sequence, such as, e.g., the 2A region of the aphthovirus foot-and-mouth disease virus (FMDV) polyprotein, which is an 18 amino acid sequence. Additional examples of 2A-like sequences that may be used include insect virus polyproteins, the NS34 protein of type C rotaviruses, and repeated sequences in *Trypanosoma* spp., as described, for example, in Donnelly et al., Journal of General Virology. 82:1027-1041, 2001.

Suitable protease cleavages sites and self-cleaving peptides are known to the skilled person (see, e.g., Ryan et al., J. Gener. Virol. 78:699-722, 1997; and Scymczak et al., Nature Biotech. 5:589-594, 2004). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are included in some embodiments, e.g., EXXYXQ(G/S) (SEQ ID NO: 42), for example, ENLYFQG (SEQ ID NO: 43) and ENLYFQS (SEQ ID NO: 44), wherein X represents any amino acid (cleavage by TEV occurs between Q and G or Q and S).

Further examples of enzymatically degradable linkers suitable for use in particular embodiments include, but are not limited to: an amino acid sequence cleaved by a serine protease such as thrombin, chymotrypsin, trypsin, elastase, kallikrein, or subtilisin. Illustrative examples of thrombin-cleavable amino acid sequences include, but are not limited to: -Gly-Arg-Gly-Asp-(SEQ ID NO: 45), -Gly-Gly-Arg-, -Gly-Arg-Gly-Asp-Asn-Pro-(SEQ ID NO: 46), -Gly-Arg-Gly-Asp-Ser-(SEQ ID NO: 47), -Gly-Arg-Gly-Asp-Ser-Pro-Lys-(SEQ ID NO: 48), -Gly-Pro-Arg-, -Val-Pro-Arg-, and -Phe-Val-Arg-. Illustrative examples of elastase-cleavable amino acid sequences include, but are not limited to: -Ala-Ala-Ala-, -Ala-Ala-Pro-Val-(SEQ ID NO: 49), -Ala-Ala-Pro-Leu-(SEQ ID NO: 50), -Ala-Ala-Pro-Phe-(SEQ ID NO: 51), -Ala-Ala-Pro-Ala-(SEQ ID NO: 52), and -Ala-Tyr-Leu-Val-(SEQ ID NO: 53).

Enzymatically degradable linkers also include amino acid sequences that can be cleaved by a matrix metalloproteinase such as collagenase, stromelysin, and gelatinase. Illustrative examples of matrix metalloproteinase-cleavable amino acid sequences include, but are not limited to: -Gly-Pro-Y-Gly-Pro-Z-(SEQ ID NO: 54), -Gly-Pro-, Leu-Gly-Pro-Z-(SEQ ID NO: 55), -Gly-Pro-Ile-Gly-Pro-Z-(SEQ ID NO: 56), and -Ala-Pro-Gly-Leu-Z-(SEQ ID NO: 57), where Y and Z are amino acids. Illustrative examples of collagenase-cleavable amino acid sequences include, but are not limited to: -Pro-Leu-Gly-Pro-D-Arg-Z-(SEQ ID NO: 58), -Pro-Leu-Gly-Leu-Leu-Gly-Z-(SEQ ID NO: 59), -Pro-Gln-Gly-Ile-Ala-Gly-Trp-(SEQ ID NO: 60), -Pro-Leu-Gly-Cys(Me)-His-(SEQ ID NO: 61), -Pro-Leu-Gly-Leu-Tyr-Ala-(SEQ ID NO: 62), -Pro-Leu-Ala-Leu-Trp-Ala-Arg-(SEQ ID NO: 63), and -Pro-Leu-Ala-Tyr-Trp-Ala-Arg-(SEQ ID NO: 64), where Z is an amino acid. An illustrative example of a stromelysin-cleavable amino acid sequence is -Pro-Tyr-Ala-Tyr-Tyr-Met-Arg-(SEQ ID NO: 65); and an example of a gelatinase-cleavable amino acid sequence is -Pro-Leu-Gly-Met-Tyr-Ser-Arg-(SEQ ID NO: 66).

Enzymatically degradable linkers suitable for use in particular embodiments include amino acid sequences that can be cleaved by an angiotensin converting enzyme, such as, for example, -Asp-Lys-Pro-, -Gly-Asp-Lys-Pro-(SEQ ID NO: 67), and -Gly-Ser-Asp-Lys-Pro-(SEQ ID NO: 68).

Enzymatically degradable linkers suitable for use in particular embodiments include amino acid sequences that can be degraded by cathepsin B, such as, for example, Val-Cit, Ala-Leu-Ala-Leu-(SEQ ID NO: 69), Gly-Phe-Leu-Gly-(SEQ ID NO: 70) and Phe-Lys.

In certain embodiments, however, any one or more of the peptide linkers are optional. For instance, linker sequences may not required when the first and second polypeptides have non-essential N-terminal and/or C-terminal amino acid regions that can be used to separate the functional domains and prevent steric interference.

The ulinastatin fusion polypeptides can be used in any of the compositions, methods, and/or kits described herein.

Polynucleotides, Expression Vectors, and Host Cells

Certain embodiments relate to polynucleotides that encode a ulinastatin fusion polypeptide, as described herein. Thus, certain embodiments include a polynucleotide that encodes any one or more of the individual ulinastatin fusion polypeptides in Table U1 or Table U2, including variants and/or fragments thereof. For instance, certain polynucleotides encode a ulinastatin fusion polypeptide that comprises, consists, or consists essentially of an amino acid sequence that is at least 80, 85, 90, 95, 96, 97, 98, 99, or 100% identical to a reference amino sequence selected from Table U1 or Table U2.

Exemplary nucleic acid coding sequences are provided in Table U3 below.

tatin fusion polypeptide, wherein the polynucleotide comprises, consists, or consists essentially of a nucleic acid sequence that is at least 80, 85, 90, 95, 96, 97, 98, 99, or 100% to a nucleic acid sequence from Table U3 (e.g., SEQ ID NO: 8 or 9).

Among other uses, these and related embodiments may be utilized to recombinantly produce ulinastatin polypeptides in a host cell. It will be appreciated by those of ordinary skill in the art that, as a result of the degeneracy of the genetic code, there are many nucleotide sequences that encode a polypeptide described herein. Some of these polynucleotides may bear minimal homology to the nucleotide sequence of any native gene. Nonetheless, polynucleotides that vary due to differences in codon usage are specifically contemplated, for example, polynucleotides that are optimized for human, yeast, or bacterial codon selection.

As will be recognized by the skilled artisan, polynucleotides may be single-stranded (coding or antisense) or double-stranded, and may be DNA (genomic, cDNA or synthetic) or RNA molecules. Polynucleotides may comprise a native sequence or may comprise a variant, or a biological functional equivalent of such a sequence. Polynucleotide variants may contain one or more substitutions, additions, deletions and/or insertions, as described herein, preferably such that the activity of the variant polypeptide is not substantially diminished relative to the unmodified polypeptide.

Additional coding or non-coding sequences may, but need not, be present within a polynucleotide, and a polynucleotide

TABLE U3

Exemplary Coding Sequences

| Description | Sequence | SEQ ID NO: |
|---|---|---|
| FL Human S10A Mutation with Signal Sequence (underlined) Ulinastatin | <u>ATGATGTCCTTTGTCTCTCTGCTCCTGGTTGGCATCCTATTCCATGCCAC CCAGGCC</u>GGCCCTGTGCCAGCTCCGCCCGACAACATCCAAGTGCAGGAAA ACTTCAATATCTCTCGGATCTATGGGAAGTGGTACAACCTGGCCATCGGT TCCACCTGCCCCTGGCTGAAGAAGATCATGGACAGGATGACAGTGAGCAC GCTGGTGCTGGGAGAGGGCGCTACAGAGGCGGAGATCAGCATGACAAGCA CTCGTTGGCGGAAAGGTGTCTGTGAGGAGACGTCTGGAGCTTATGAGAAA ACAGATACTGACGGGAAGTTTCTCTATCACAAATCCAAATGGAATATAAC CATGGAGTCCTATGTGGTCCACACCAACTATGATGAGTATGCCATTTTCC TGACAAAGAAATTCAGCCGCCATCACGGACCCACCATTACTGCCAAGCTC TACGGGCGGGCGCCGCAGCTGAGGGAAACTCTCCTGCAGGACTTCAGAGT GGTTGCCCAGGGTGTGGGCATCCCTGAGGACTCCATCTTCACCATGGCTG ACCGAGGCGAATGTGTCCCAGGGGAGCAGGAACCAGAGCCCATCTTAATC CCGAGAGTCCGGAGGGCTGTGCTACCCCAAGAAGAGGAAGGAGCTGGGGG TGGGCAACTGGTAACTGAAGTCACCAAGAAAGAAGATTCCTGCCAGCTGG GCTACTCGGCCGGTCCCTGTATGGGAATGACCAGCAGATATTTCTATAAT GGAACATCCATGGCCTGTGAGACTTTCCAGTACGGCGGCTGCATGGGAAA CGGCAACAACTTCGTCACAGAAAAGGAGTGTCTGCAGACCTGCCGAACTG TGGCGGCCTGCAATCTCCCCATCGTCCGGGGCCCCTGCCGAGCCTTCATC CAGCTCTGGGCATTTGATGCTGTCAAGGGGAAGTGCGTCCTCTTCCCCTA CGGGGGCTGCCAGGGCAACGGGAACAAGTTCTACTCAGAGAAGGAGTGCA GAGAGTACTGCGGTGTCCCTGGTGATGGTGATGAGGAGCTGCTGCGCTTC TCCAACTGA | 8 |
| Mature Human S10A Mutation with Signal Sequence (underlined) Ulinastatin | <u>ATGATGTCCTTTGTCTCTCTGCTCCTGGTTGGCATCCTATTCCATGCCAC CCAGGCC</u>GCTGTGCTACCCCAAGAAGAGGAAGGAGCTGGGGGTGGGCAAC TGGTAACTGAAGTCACCAAGAAAGAAGATTCCTGCCAGCTGGGCTACTCG GCCGGTCCCTGTATGGGAATGACCAGCAGATATTTCTATAATGGAACATC CATGGCCTGTGAGACTTTCCAGTACGGCGGCTGCATGGGAAACGGCAACA ACTTCGTCACAGAAAAGGAGTGTCTGCAGACCTGCCGAACTGTGGCGGCC TGCAATCTCCCCATCGTCCGGGGCCCCTGCCGAGCCTTCATCCAGCTCTG GCATTTGATGCTGTCAAGGGGAAGTGCGTCCTCTTCCCCTACGGGGGCT GCCAGGGCAACGGGAACAAGTTCTACTCAGAGAAGGAGTGCAGAGAGTAC TGCGGTGTCCCTGGTGATGGTGATGAGGAGCTGCTGCGCTTCTCCAACTG A | 9 |

Thus, certain embodiments include a polynucleotide, for example, an isolated polypeptide, which encodes a ulinastatin may, but need not, be linked to other molecules and/or support materials. Hence, the polynucleotides, regardless of the length of the coding sequence itself, may be combined with other DNA or RNA sequences, such as promoters, enhances, polyadenylation signals, additional restriction enzyme sites, multiple cloning sites, other coding segments, and the like, such that their overall length may vary considerably.

The polynucleotide sequences may also be of mixed genomic, cDNA, RNA, and that of synthetic origin. For example, a genomic or cDNA sequence encoding a leader peptide may be joined to a genomic or cDNA sequence encoding the polypeptide, after which the DNA or RNA sequence may be modified at a site by inserting synthetic oligonucleotides encoding the desired amino acid sequence for homologous recombination in accordance with well-known procedures or preferably generating the desired sequence by PCR using suitable oligonucleotides. In some embodiments a signal sequence can be included before the coding sequence. This sequence encodes a signal peptide N-terminal to the coding sequence which communicates to the host cell to direct the polypeptide to the cell surface or secrete the polypeptide into the media. Typically the signal peptide is clipped off by the host cell before the protein leaves the cell. Signal peptides can be found in variety of proteins in prokaryotes and eukaryotes.

One or multiple polynucleotides can encode a ulinastatin polypeptide described herein. Moreover, the polynucleotide sequence can be manipulated for various reasons. Examples include but are not limited to the incorporation of preferred codons to enhance the expression of the polynucleotide in various organisms (see generally Nakamura et al., Nuc. Acid. Res. 28:292, 2000).

Also included are expression vectors that comprise the polynucleotides, and host cells that comprise the polynucleotides and/or expression vectors. Ulinastatin polypeptides can be produced by expressing a DNA or RNA sequence encoding the polypeptide in a suitable host cell by well-known techniques. The term "host cell" is used to refer to a cell into which has been introduced, or which is capable of having introduced into it, a nucleic acid sequence encoding one or more of the polypeptides described herein, and which further expresses or is capable of expressing a polypeptide of interest, such as a polynucleotide encoding any herein described polypeptide. The term includes the progeny of the parent cell, whether or not the progeny are identical in morphology or in genetic make-up to the original parent, so long as the selected gene is present.

In some instances, a polynucleotide or expression vector comprises additional non-coding sequences. For example, the "control elements" or "regulatory sequences" present in an expression vector are non-translated regions of the vector, including enhancers, promoters, 5' and 3' untranslated regions, which interact with host cellular proteins to carry out transcription and translation. Such elements may vary in their strength and specificity. Depending on the vector system and host utilized, any number of suitable transcription and translation elements, including constitutive and inducible promoters, may be used.

Figure 2:
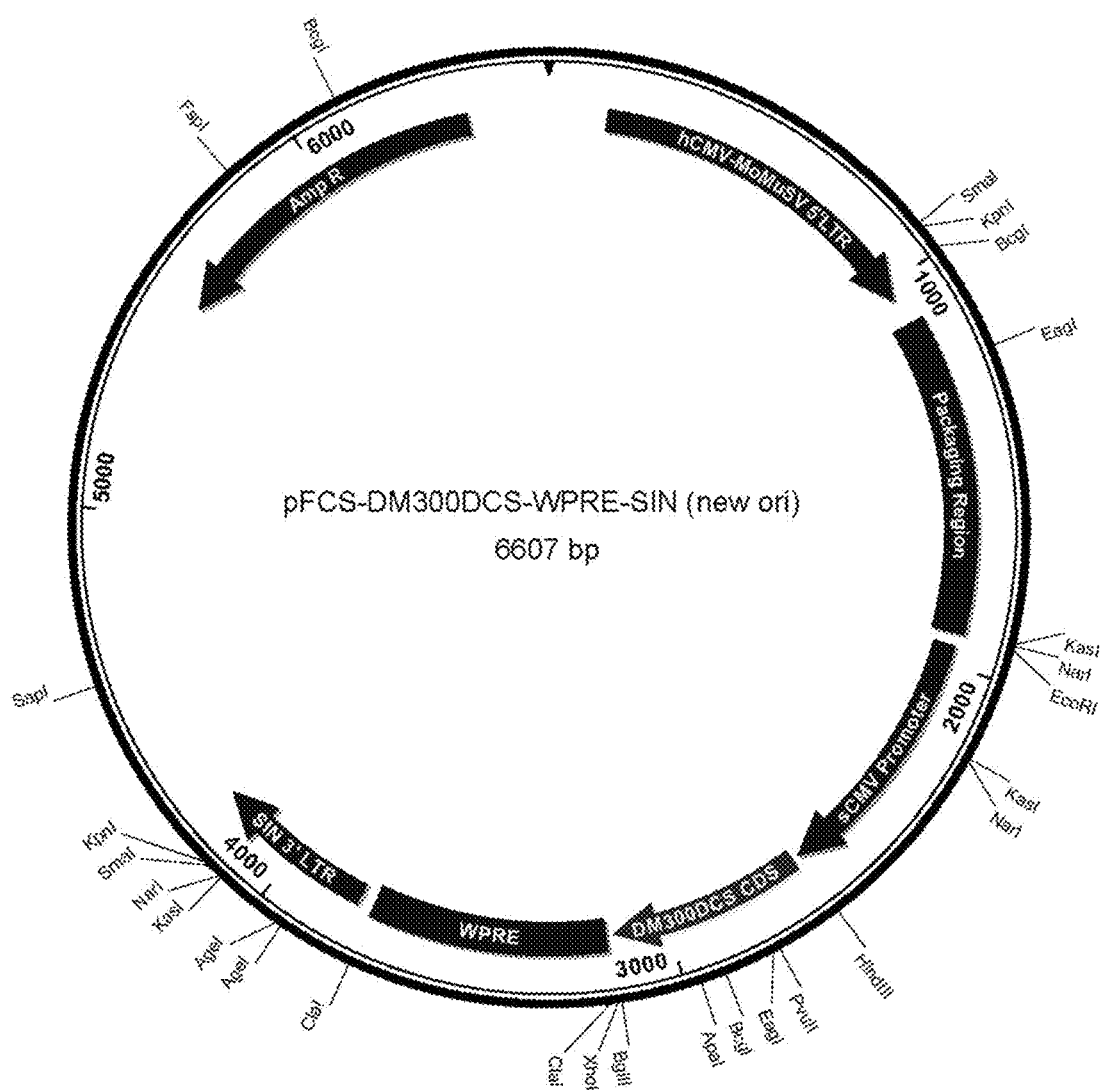
FIG. 2 shows a vector map of pFCS-DM300DCS-WPRE-SIN (new ori), GDDDA02.0002, encoding the mature ulinastatin fusion polypeptide; SEQ ID NO: 7 (polypeptide); and SEQ ID NO: 9 (nucleic acid).
Figure 3:
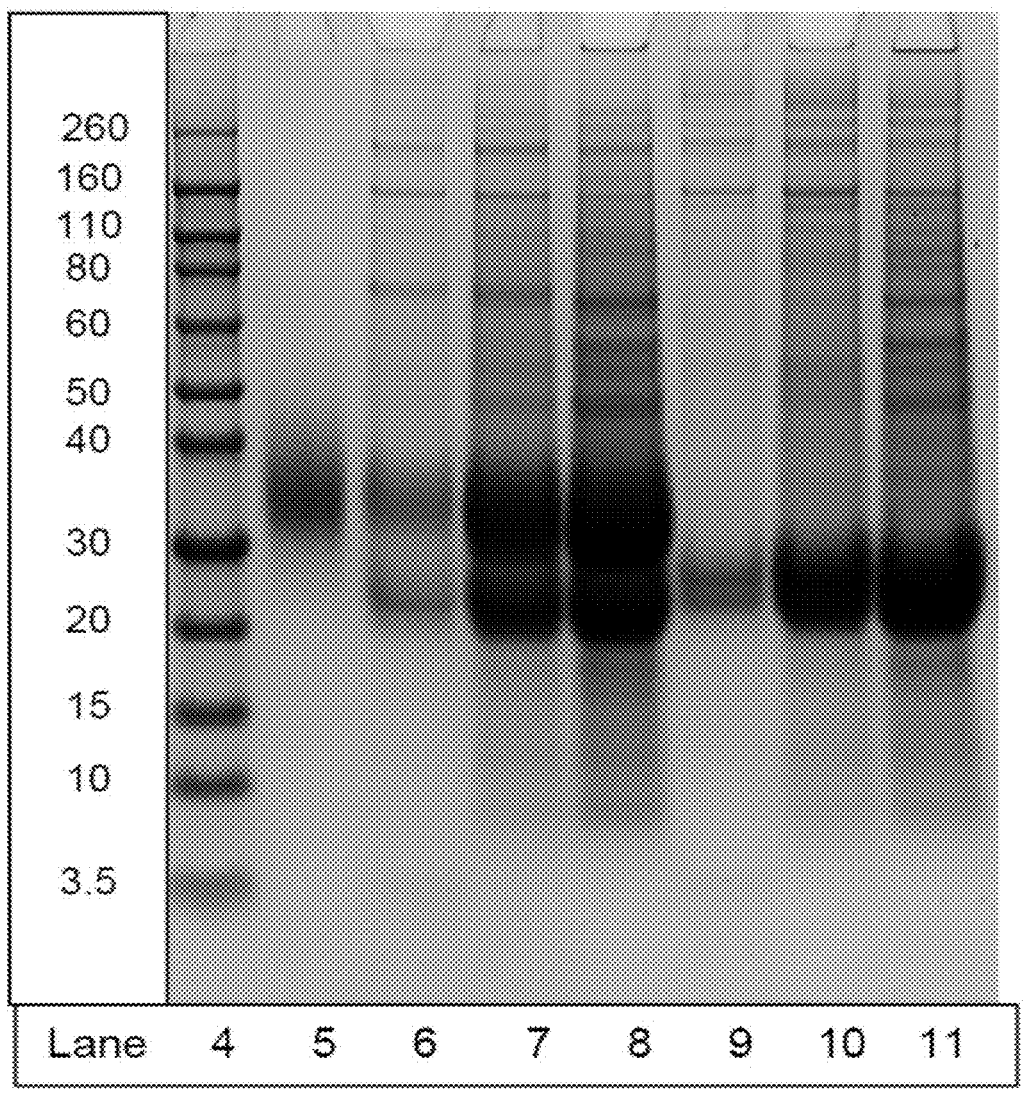
FIG. 3 shows a reducing SDS-PAGE gel analysis of the expressed ulinastatin fusion polypeptides. Lane 4: Novex Sharp Pre-Stained Standard. Lane 5: Control Ulinastatin from urine. Lane 6: Media from Day 4 of culture (Full-length Ulinastatin fusion). Lane 7: Media from Day 8 of culture (Full-length Ulinastatin fusion). Lane 8: Media from Day 12 of culture (Full-length Ulinastatin fusion). Lane 9: Media from Day 4 of culture (Mature Ulinastatin Fusion). Lane 10: Media from Day 8 of culture (Mature Ulinastatin Fusion). Lane 11: Media from Day 12 of culture (Mature Ulinastatin Fusion).

A variety of expression vector/host systems are known and may be utilized to contain and express polynucleotide sequences. These include, but are not limited to, microorganisms such as bacteria transformed with an expression vector, for example, a recombinant bacteriophage, plasmid, or cosmid DNA expression vector; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems, including mammalian cell and more specifically human cell systems transformed with viral, plasmid, episomal or integrating expression vectors. Certain embodiments therefore include an expression vector, comprising a polynucleotide sequence that encodes a polypeptide described herein, for example, a ulinastatin fusion polypeptide. In particular embodiments, the expression vector is a retroviral vector (or retrovector), for example, as illustrated in FIGS. 2-3, and Tables E1-E2.

Also included are host cells that comprise the polynucleotides and/or expression vectors. In mammalian host cells, a number of expression systems are well known in the art and commercially available. Exemplary mammalian host cells and systems include, for example, HEK293 cells, CHO cells, including GPEx® Chinese Hamster Ovary (GCHO) cell lines, HeLa cells, and others. Mammalian expression systems can utilize attached cell lines, for example, in T-flasks, roller bottles, shake flasks (e.g., 2.8 L), and/or cell factories, or suspension cultures, for example, in 1 L and 5 L spinners, 5 L, 14 L, 40 L, 100 L and 200 L stir tank bioreactors, or 20/50 L and 100/200 L WAVE bioreactors, among others known in the art. Certain therefore embodiments include a recombinant host cell, for example, a mammalian host cell, which comprises a polynucleotide that encodes a ulinastatin fusion polypeptide, as described herein. In specific embodiments, the host cell expresses or overexpresses a protease, for example, a furin polypeptide, which cleaves full-length ulinastatin to produce mature ulinastatin. Certain host cells (e.g., HEK293 cells) can be used to produce replication incompetent, high-titer retrovector particles, and certain host cells (CHO, GCHO) can be transduced with the retrovector particles to generate ulinastatin-expressing cells.

Also included are methods for recombinantly-producing a ulinastatin polypeptide, as described herein. In some embodiments, a polynucleotide or expression vector encoding a ulinastatin fusion polypeptide is introduced directly into a host cell, and the cell is incubated under conditions sufficient to induce expression of the encoded protein(s). Certain embodiments thus relate to methods for recombinantly-producing a ulinastatin polypeptide, comprising (a) expressing the ulinastatin fusion polypeptide in the recombinant mammalian host cell described herein, optionally a CHO cell or GCHO; and (b) isolating the ulinastatin polypeptide from the host cell or a medium containing the host cell, thereby recombinantly-producing the ulinastatin polypeptide. Expression of a ulinastatin polypeptide in the host cell may be achieved by culturing under appropriate conditions recombinant host cells containing the polynucleotide (see, for example, Example 1). Following production by expression, the ulinastatin polypeptide may be isolated and/or purified using any suitable technique, and then used as desired. Also, following expression of the mature ulinastatin fusion polypeptides, certain embodiments comprise the step of cleaving the signal peptide, for example, with a protease.

The ulinastatin polypeptides produced by a recombinant host cell can be purified and characterized according to a variety of techniques known in the art. Exemplary systems for performing protein purification and analyzing protein purity include fast protein liquid chromatography (FPLC) (e.g., AKTA and Bio-Rad FPLC systems), high-performance liquid chromatography (HPLC) (e.g., Beckman and Waters HPLC). Exemplary chemistries for purification include ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HYPERD® ion exchange chromatography, and hydrophobic interaction columns (HIC), among others known in the art. See also the Examples.

Also included are methods of assessing or measuring the activity of the produced and purified ulinastatin polypeptide under physiological conditions, optionally of temperature and pH, wherein the ulinastatin polypeptide has activity under the physiological conditions. In some embodiments, the ulinastatin polypeptide has at least about 50, 60, 70, 80, 90, 100, 200, 300, 400, 500, 600, 700, 800, 900, 1000% or more of the activity relative to an ulinastatin polypeptide of SEQ ID NO: 2 (mature human ulinastatin) under comparable physiological conditions.

Certain aspects further comprise preparing a composition that comprises the ulinastatin polypeptide, for example, wherein the composition has a purity of at least about 80%, 85%, 90%, 95%, 98%, or 99% on a protein basis or a weight-weight basis, and wherein the composition is substantially aggregate-free and substantially endotoxin-free.

Compositions and Methods of Use

Certain embodiments include therapeutic compositions comprising a ulinastatin polypeptide, for example, a ulinastatin polypeptide produced according to the methods described herein, and methods of using the same for the treatment of various diseases.

Some embodiments include compositions, for example, therapeutic or pharmaceutical compositions, comprising a mature ulinastatin polypeptide described herein, including a ulinastatin polypeptide prepared or produced according to the methods described herein, and a pharmaceutically-acceptable carrier. For instance, certain compositions comprise mature ulinastatin polypeptide with a T17-O-linked glycan, comprising (i) a modified O-linked glycosylation site at residues Glu-Gly-Ser-Gly (SEQ ID NO: 10) which reduces glycosylation at the O-linked glycosylation site, (ii) an N-linked glycan at residue at residue N45, and (iii) an O-linked glycan at residue T17, the residues being defined by SEQ ID NO: 2 or 4, as described herein, and a pharmaceutically-acceptable carrier. Specific examples of mature ulinastatin polypeptides, and active variants and fragments thereof, are described herein (see, for example, Table U1 and related disclosure)

Certain compositions comprise a mixture of ulinastatin glycoforms. For example, certain compositions comprise (a) a first mature ulinastatin polypeptide comprising the T17-O-linked glycan, as described herein, and (b) a second mature ulinastatin polypeptide, which comprises the N-linked glycan at residue N45 and does not comprise the O-linked glycan at residue T17. In some embodiments, the second mature ulinastatin polypeptide has a modified O-linked glycosylation site at residues Glu-Gly-Ser-Gly (SEQ ID NO: 10), as described herein, for example, the S10A substitution, which reduces glycosylation at the O-linked glycosylation site. In some embodiments, the second, mature ulinastatin polypeptide of (b) comprises, consists, or consists essentially of an amino acid sequence that is at least 80, 85, 90, 95, 96, 97, 98, 99, or 100% identical to SEQ ID NO: 2 or 4, comprises or retains the modified O-linked glycosylation site (e.g., the S10A substitution) and the N-linked glycan at residue N45, does not comprise the O-linked glycan at residue T17, and has at least one ulinastatin activity.

In some embodiments, the mature ulinastatin polypeptides of (a):(b) are present in the composition at a ratio ranging from about 20:1 to about 1:20, optionally about 20:1, 15:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:15, or 1:20.

Certain compositions are substantially pure on a protein basis or weight-basis. For instance, as above, certain compositions have a purity of at least about 80%, 85%, 90%, 95%, 98%, or 99% on a protein basis or a weight-weight basis and are substantially aggregate-free, for example, less than about 10, 9, 8, 7, 6, or 5% aggregated. Certain compositions are substantially endotoxin-free, as described herein.

The compositions may be prepared by methodology well known in the pharmaceutical art. For example, a composition intended to be administered by injection can be prepared by combining a composition that comprises a ulinastatin polypeptide, as described herein, and optionally one or more of buffers or excipients, optionally with sterile, distilled water so as to form a solution. Certain compositions comprise a physiological saline solution (e.g., 0.9% normal saline) or dextrose (e.g., about 1-10% dextrose, or 1, 2, 3, 4, 5, 6, 7, 8, 9, or 10% dextrose). A surfactant can be added to facilitate the formation of a homogeneous solution or suspension. Surfactants are compounds that non-covalently interact with the ulinastatin polypeptide in the composition so as to facilitate dissolution or homogeneous suspension of the polypeptide in the aqueous delivery system.

Certain compositions are at a pharmaceutically-acceptable pH. For instance, in certain embodiments, the pharmaceutically-acceptable pH is about 5.0 to about 8.0 (±0.01 to ±0.1), or about 5.0, 5.1, 5.2, 5.3, 5.4, 5.5, 5.6, 5.7, 5.8, 5.9, 6.0, 6.1. 6.2. 6.3. 6.4. 6.5. 6.6. 6.7. 6.8. 6.9. 7.0, 7.1, 7.2, 7.3, 7.4, 7.5, 7.6, 7.7, 7.8, 7.9, or 8.0 (±0.01 to ±0.1), including all integers and ranges in between.

In certain embodiments, a ulinastatin polypeptide has at least one ulinastatin activity at a pH close to the physiological pH of human blood. Thus, in some embodiments, a ulinastatin polypeptide has at least one ulinastatin activity at a pH of about 4 to about 10.8, or about 6 to about 8, or about 6.5 to about 7.5. In certain embodiments, a ulinastatin polypeptide has effective ulinastatin activity at about pH 7.4.

In specific embodiments, the composition has one or more of the following determinations of purity: less than about 1 EU endotoxin/mg protein, less that about 100 ng host cell protein/mg protein, less than about 10 pg host cell DNA/mg protein, and/or is substantially aggregate-free.

Also included are methods of treating, ameliorating the symptoms of, or inhibiting the progression of, a disease in a subject in need thereof, comprising administering to the subject a composition comprising at least one ulinastatin polypeptide produced according to the methods described herein.

The methods and compositions described herein can be used in the treatment of any variety of diseases or conditions. For instance, certain embodiments include methods of treating an inflammatory disease or condition in a subject in need thereof, comprising administering to the subject a therapeutic composition described herein.

Exemplary inflammatory diseases or conditions include pancreatitis (e.g., acute pancreatitis, chronic pancreatitis, endoscopic retrograde cholangiopancreatography (ERCP)-induced pancreatitis), systemic inflammation, colitis, autoimmune encephalomyelitis, Stevens-Johnson syndrome, arthritis, renal failure, burns, sepsis/septic shock including severe sepsis and related pro-inflammatory/secondary conditions (e.g., organ failure), systemic inflammatory response syndrome (SIRS), toxic epidermal necrolysis (TEN), Kawasaki disease, kidney disease (e.g., acute kidney failure, chronic kidney disease), ischemic conditions (e.g., ischemia-reperfusion injury in the liver, kidney, heart, lungs, brain), lung inflammation and inflammatory lung conditions (e.g., pulmonary infection, pneumonia, including infectious interstitial pneumonia associated with mixed connective tissue disease, pulmonary fibrosis, acute respiratory distress syndrome), liver inflammation including hepatitis, anaphylaxis, post-operative or post-surgical complications (e.g., renal function, cardiac surgery, lung surgery, cognitive dysfunction, liver transplantation), lipopolysaccharide (LPS)-induced inflammation or tissue injury (e.g., lungs, liver, brain), inflammation or dysfunction secondary to diabetes (e.g., diabetes-induced cardiac dysfunction), burn injury, heat stroke, inflammatory or neuropathic pain, acute poisoning, hyperlipidemia-associated inflammation, autoimmunity-associated inflammation, allogeneic transplant or blood transfusion-associated inflammation, and neuroinflammation.

Also included are methods of treating, ameliorating the symptoms of, or inhibiting the progression of, a cancer in a subject in need thereof, comprising administering to the subject a therapeutic composition described herein. The methods and therapeutic compositions described herein can be used in the treatment of any variety of cancers or tumors. In some embodiments, the cancer is a primary cancer, i.e., a cancer growing at the anatomical site where tumor progression began and yielded a cancerous mass. In some embodiments, the cancer is a secondary or metastatic cancer, i.e., a cancer which has spread from the primary site or tissue of origin into one or more different sites or tissues. In some embodiments, the subject has a cancer selected from one or more of melanoma (e.g., metastatic melanoma), pancreatic cancer, bone cancer, prostate cancer, small cell lung cancer, non-small cell lung cancer (NSCLC), mesothelioma, leukemia (e.g., lymphocytic leukemia, chronic myelogenous leukemia, acute myeloid leukemia, relapsed acute myeloid leukemia), lymphoma, hepatoma (hepatocellular carcinoma), sarcoma, B-cell malignancy, breast cancer, ovarian cancer, colorectal cancer, glioma, glioblastoma multiforme, meningioma, pituitary adenoma, vestibular schwannoma, primary CNS lymphoma, primitive neuroectodermal tumor (medulloblastoma), kidney cancer (e.g., renal cell carcinoma), bladder cancer, uterine cancer, esophageal cancer, brain cancer, head and neck cancers, cervical cancer, testicular cancer, thyroid cancer, and stomach cancer.

In some embodiments, as noted above, the cancer or tumor is a metastatic cancer. Further to the above cancers, exemplary metastatic cancers include, without limitation, bladder cancers which have metastasized to the bone, liver, and/or lungs; breast cancers which have metastasized to the bone, brain, liver, and/or lungs; colorectal cancers which have metastasized to the liver, lungs, and/or peritoneum; kidney cancers which have metastasized to the adrenal glands, bone, brain, liver, and/or lungs; lung cancers which have metastasized to the adrenal glands, bone, brain, liver, and/or other lung sites; melanomas which have metastasized to the bone, brain, liver, lung, and/or skin/muscle; ovarian cancers which have metastasized to the liver, lung, and/or peritoneum; pancreatic cancers which have metastasized to the liver, lung, and/or peritoneum; prostate cancers which have metastasized to the adrenal glands, bone, liver, and/or lungs; stomach cancers which have metastasized to the liver, lung, and/or peritoneum; thyroid cancers which have metastasized to the bone, liver, and/or lungs; and uterine cancers which have metastasized to the bone, liver, lung, peritoneum, and/or vagina; among others.

In some instances, administration of a therapeutic composition reduces inflammation or one or more inflammatory responses in the subject. For example, in some instances the administration a therapeutic composition reduces one or more of endothelial activation/damage, proinflammatory cytokine and chemokine production/release (for example, IL-1β, MIP-1α, MCP-1, and CXCL1), fibrinogen synthesis, neutrophil recruitment into organs, and/or organ injury in the subject.

In some embodiments, the methods or compositions described herein increase median survival time of a patient by 4 weeks, 5 weeks, 6 weeks, 7 weeks, 8 weeks, 9 weeks, 10 weeks, 15 weeks, 20 weeks, 25 weeks, 30 weeks, 40 weeks, or longer. In certain embodiments, the methods or compositions described herein increase median survival time of a patient by 1 year, 2 years, 3 years, or longer.

In certain embodiments, for example, in the treatment of cancer, the composition administered is sufficient to result in tumor regression, as indicated by a statistically significant decrease in the amount of viable tumor, for example, at least a 10%, 20%, 30%, 40%, 50% or greater decrease in tumor mass, or by altered (e.g., decreased with statistical significance) scan dimensions. In certain embodiments, the composition administered is sufficient to result in stable disease. In certain embodiments, the composition administered is sufficient to result in stabilization or clinically relevant reduction in symptoms of a particular disease indication known to the skilled clinician.

Methods for identifying subjects with one or more of the diseases or conditions described herein are known in the art.

Administration may be achieved by a variety of different routes. Modes of administration depend upon the nature of the condition to be treated or prevented. For example, a composition can be administered orally, intranasally, intraperitoneally, parenterally, intravenously, intralymphatically, intratumorly, intramuscularly, interstitially, intraintestinally, intra-arterially, subcutaneously, intraocularly, intrasynovial, transepithelial, and/or transdermally Particular embodiments include administration by IV infusion.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

In some embodiments, a therapeutically effective amount or therapeutic dosage of a composition described herein is an amount that is effective to reduce inflammation or an inflammatory response in a subject. In certain instances, treatment is initiated with small dosages which can be increased by small increments until the optimum effect under the circumstances is achieved.

In some embodiments, a dosage is administered from about once a day to about once every two or three weeks. For example, in certain embodiments, a dosage is administered about once every 1, 2, 3, 4, 5, 6, or 7 days, or about once a week, or about twice a week, or about three times a week, or about once every two or three weeks.

Certain embodiments comprise administering a ulinastatin polypeptide at a dosage (e.g., a daily dosage) of about $1 \times 10^4$ U to about $1 \times 10^5$ U to about $100 \times 10^5$ U, or about $1\times10^4$ U, $2\times10^4$ U, $3\times10^4$ U, $4\times10^4$ U, $5\times10^4$ U, $6\times10^4$ U, $7\times10^4$ U, $8\times10^4$ U, $9\times10^4$ U, $1\times10^5$ U, $2\times10^5$ U, $3\times10^5$ U, $4\times10^5$ U, $5\times10^5$ U, $6\times10^5$ U, $7\times10^5$ U, $8\times10^5$ U, $9\times10^5$ U, $10\times10^5$ U, $11\times10^5$ U, $12\times10^5$ U, $15\times10^5$ U, $20\times10^5$ U, $30\times10^5$ U, $40\times10^5$ U, $50\times10^5$ U, $60\times10^5$ U, $70\times10^5$ U, $80\times10^5$ U, or $100\times10^5$ U, including all ranges and integers in between. Certain embodiments comprise administering a ulinastatin polypeptide at a dosage (e.g., a daily dosage) of about, at least about, or no more than about, 50,000 U/kg, 125,000 U/kg, 250,000 U/kg, 500,000 U/kg, 750,000 U/kg, or 1,000,000 U/kg; or ranging from about 50,000-1,000,000 U/kg, about 125,000-1,000,000 U/kg, about 250,000-1,000,000 U/kg, about 500,000-1,000,000 U/kg, about 750,000-1,000,000 U/kg, about 50,000-750,000 U/kg, about 125,000-750,000 U/kg, about 250,000-750,000 U/kg, about 500,000-750,000 U/kg, about 50,000-500,000 U/kg, about 125,000-500,000 U/kg, about 250,000-500,000 U/kg, about 50,000-250,000 U/kg, about 125,000-250,000 U/kg, or about 50,000-125,000 U/kg.

Certain embodiments comprising administering a subcutaneous dosage. Some embodiments include administering an intravenous dosage, for example, by infusing the daily dosage intravenously over about a 1, 2, or 3 hour period. Particular embodiments comprise infusing the daily dosage over about a 1, 2, or 3 hour period, optionally about 1, 2, or 3 times per day, and optionally for about 2, 3, 4, 5, 6, or 7 or more days in a row.

Also included are patient care kits, comprising one or more compositions or ulinastatin polypeptides produced according to the methods described herein. Certain kits also comprise one or more pharmaceutically-acceptable diluents or solvents, such as water (e.g., sterile water) or saline. In some embodiments, the compositions or ulinastatin polypeptides are stored in vials, cartridges, dual chamber syringes, and/or pre-filled mixing systems.

The kits herein may also include a one or more additional therapeutic agents or other components suitable or desired for the indication being treated, or for the desired diagnostic application. The kits herein can also include one or more syringes or other components necessary or desired to facilitate an intended mode of delivery (e.g., stents, implantable depots, etc.).

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Preparation and Expression of Ulinastatin Fusion Polypeptides

Two fusion constructs were prepared to obtain optimal ulinastatin expression in Chinese hamster ovary (CHO) cells. The bovine alpha-lactalbumin signal peptide was fused to the N-terminus of full-length human ulinastatin, and also to the mature form of human ulinastatin. Each of the ulinastatin sequences were modified to incorporate a serine to alanine mutation at residue ten (S10A) of the mature ulinastatin sequence to prevent glycosaminoglycan attachment at that residue. The full-length ulinastatin fusion polypeptide requires enzyme cleavage (furin) in the CHO cells to produce mature ulinastatin. The mature ulinastatin fusion polypeptide requires only cleavage of the bovine alpha-lactalbumin signal peptide to produce mature ulinastatin. The amino acid sequences of the fusion polypeptides are shown in Table U2, and the nucleic acid coding sequences are shown in Table U3. The DNA sequences were confirmed by DNA sequencing.

Retroviral Vector Production.

The fusion protein constructs outlined above were introduced into retroviral vectors, as illustrated in FIG. 2 (FL ulinastatin) and FIG. 3 (mature ulinastatin). The details of the vector components are provided in Table E1 and Table E2 below.

TABLE E1

Retrovector components of FL ulinastatin fusion construct
pFCS-DM300FL-WPRE-SIN (new ori), GDDDA01.0002

| Component | Description | Function |
| --- | --- | --- |
| 5' hCMV-MoMuSV LTR (R-U5) bp 149-865 hCMV promoter bp 866-1041 MoMuSV R-U5 | A fusion of the full-length human CMV promoter to the R-U5 regions of the Moloney Murine Sarcoma Virus 5' LTR | The human cytomegalovirus IE promoter has strong constitutive activity in most mammalian cells. Used to create high titer of retrovector particles when transfected into packaging cells. The hCMV promoter is lost after the packaging cell step. |
| Extended packaging region bp 1111-1920 | MoMuLV/SV packaging region from the LTR through a mutated ATG site in the MLV Gag gene | Packaging region allows creation of retrovector particles by allowing RNA to associate with MoMuLV Gag/Pol gene products. |
| sCMV promoter bp 1952-2624 | The immediate early promoter from simian CMV | Alternative strong constitutive promoter to drive expression of product gene. |

TABLE E1-continued

Retrovector components of FL ulinastatin fusion construct
pFCS-DM300FL-WPRE-SIN (new ori), GDDDA01.0002

| Component | Description | Function |
|---|---|---|
| DM300FL CDS bp 2640-3698 | DM300FL CDS including the signal peptide sequence | Complete DM300FL CDS was synthesized and cloned by restriction digestion. |
| WPRE bp 3717-4317 | A fragment from the woodchuck Hepatitis B virus Pol gene | Region that is thought to aid export of unspliced RNA and improve protein expression. |
| SIN 3' LTR bp 4358-4781 | The 3' LTR from MoMuLV | Functions as a Poly A signal for RNA. Allows reverse transcription and DNA insertion of retrovector into mammalian cells from retrovector particles. In proviral DNA deletion in U3 region is duplicated to 5' LTR hereby inactivating 5' LTR promoter activity. |
| Plasmid backbone- *Escherichia coli* origin of replication and β-lactamase gene for ampicillin resistance bp 6100-6960 bp 1-148 | Basic *E. coli* plasmid sequences | Allows selection of plasmid containing bacteria in *E. coli* and replication of DNA in *E. coli*. These regions are lost after transfecting plasmids into packaging cells and creating retrovector particles. |

TABLE E2

Retrovector components of mature ulinastatin fusion construct
pFCS-DM300DCS-WPRE-SIN (new ori), GDDDA02.0002

| Component | Description | Function/Notes |
|---|---|---|
| 5' hCMV-MoMuSV LTR (R-U5) bp 149-865 hCMV promoter bp 866-1041 MoMuSV R-U5 | A fusion of the full-length human CMV promoter to the R-U5 regions of the Moloney Murine Sarcoma Virus 5' LTR | The human cytomegalovirus IE promoter has strong constitutive activity in most mammalian cells. Used to create high titer of retrovector particles when transfected into packaging cells. The hCMV promoter is lost after the packaging cell step. |
| Extended packaging region bp 1111-1920 | MoMuLV/SV packaging region from the LTR through a mutated ATG site in the MLV Gag gene | Packaging region allows creation of retrovector particles by allowing RNA to associate with MoMuLV Gag/Pol gene products. |
| sCMV promoter bp 1952-2624 | The immediate early promoter from simian CMV | Alternative strong constitutive promoter to drive expression of product gene. |
| DM300DCS CDS bp 2640-3140 | DM300DCS CDS including the signal peptide sequence | Complete DM300DCS CDS was synthesized and cloned by restriction digestion. |
| WPRE bp 3159-3759 | A fragment from the woodchuck Hepatitis B virus Pol gene | Region that is thought to aid export of unspliced RNA and improve protein expression. |
| SIN 3' LTR bp 3800-4223 | The 3' LTR from MoMuLV | Functions as a Poly A signal for RNA. Allows reverse transcription and DNA insertion of retrovector into mammalian cells from retrovector particles. In proviral DNA deletion in U3 region is duplicated to 5' LTR hereby inactivating 5' LTR promoter activity. |
| Plasmid backbone- *Escherichia coli* origin of replication and β-lactamase gene for ampicillin resistance bp 5542-6402 bp 1-148 | Basic *E. coli* plasmid sequences | Allows selection of plasmid containing bacteria in *E. coli* and replication of DNA in *E. coli*. These regions are lost after transfecting plasmids into packaging cells and creating retrovector particles. |

The retrovectors were transfected into a HEK293 cell line that constitutively produces the MLV gag, pro, and pol proteins. An envelope-containing expression plasmid was also co-transfected with each of the two retrovector constructs. The two co-transfections resulted in the production of replication incompetent high titer retrovectors for each of the two gene constructs, which was concentrated by ultracentrifugation and used for cell transductions (see Bleck, An alternative method for the rapid generation of stable, high-expressing mammalian cell lines, Bioprocessing J. September/October pp 1-7, 2005; and Bleck, GPEx® A Flexible Method for the Rapid Generation of Stable, High Expressing, Antibody Producing Mammalian Cell Lines Chapter 4 In: Current Trends in Monoclonal Antibody Development and Manufacturing, Biotechnology: Pharmaceutical Aspects, Edited by: S. J. Shire et al. © 2010 American Association of Pharmaceutical Scientists, DOI 10.1007/978-0-387-76643-0_4).

Pooled cell lines for each retroviral construct were produced by three cycles of cell transduction of the GPEx® Chinese Hamster Ovary (GCHO) parental cell line with the replication incompetent, high-titer retrovectors. The full-length ulinastatin retrovector was transduced into a GCHO cell line that overexpresses a furin enzyme, which digests the full-length molecule to produce mature ulinastatin. The mature ulinastatin retrovectors were transduced into normal GCHO cells.

Post-transduction, the pooled cell lines for each of the two constructs was scaled up for production in a fed batch study in 2.8 L shake flasks. Each shake flask was seeded with 300,000 viable cells per mL in G12.1 media (Irvine Scientific) and incubated in a humidified (70-80%) shaking incubator at 80 rpm with 5% $CO_2$ and a temperature of 37° C. Cultures were fed seven times during the production run using two different feed supplements. Culture temperature was decrease from 37° C. to 34° C. on day 5 of the culture. Cultures were terminated when viabilities were ≤80%.

Confirmation of protein production was determined by reducing SDS-PAGE gel analysis, as shown in FIG. 3. The ulinastatin control from urine contains both N-linked glycosylation and glycosaminoglycan (GAG) molecules. The full-length and the mature ulinastatin fusion constructs should only have the N-linked glycosylation because the attachment site for the GAG molecules was mutated. The full-length ulinastatin samples appear to have been fully-cleaved by the added furin in the cell line. The gel shows both the large fragment of the cleaved protein (186 amino acids and 2 N-linked glycosylation sites (Upper band)) and the mature ulinastatin fragment (147 amino acids and one N-linked glycosylation site (lower band)).

The mature ulinastatin samples contain only the smaller sized, mature ulinastatin fragment. The lower molecular weight, mature ulinastatin product appears to be composed of two bands when run on a reducing SD S-PAGE gel. This doublet was not observed for the full-length sample (see FIG. 3, comparing lane 6 to lane 9).

Figure 4:
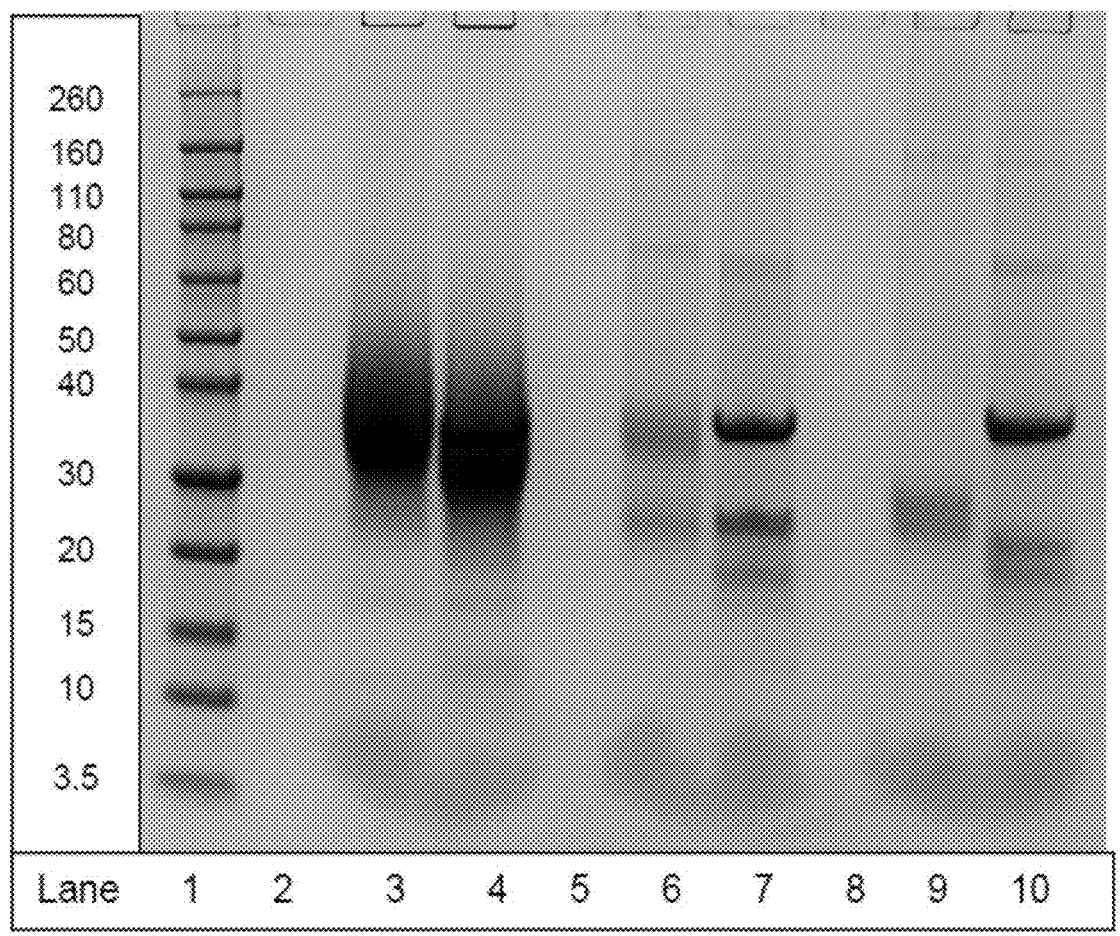
FIG. 4 shows a reducing SDS-PAGE gel analysis of the expressed ulinastatin fusion polypeptides. Lane 1: Novex Sharp Pre-Stained Standard. Lane 2: empty. Lane 3: Control Ulinastatin from urine. Lane 4: Control Ulinastatin from urine (PNGase treated). Lane 5: empty. Lane 6: Full-length ulinastatin. Lane 7: Full-length ulinastatin (PNGase treated). Lane 8: empty. Lane 9: Mature ulinastatin. Lane 10: Mature ulinastatin (PNGase treated).

To investigate the two bands observed for the mature ulinastatin sample in lane 9 of FIG. 3, the material was first examined to determine if the second band was due to N-linked glycosylation. Here, the urine derived ulinastatin, the full-length ulinastatin, and the mature ulinastatin samples were digested with PNGase to remove any potential N-linked glycans, and then run on a gel. If the doublet was caused by N-linked glycosylation, PNGase digestion would be expected to result in a single band on a reducing SDS-PAGE gel. However, as shown in FIG. 4, PNGase digestion did not change the doublet observed in the mature ulinastatin sample (see Lane 10). Instead, the N-linked glycan was removed, causing the shift in molecular weight (compare Lanes 9 and 10 in FIG. 4), but the doublet was maintained, signifying that an additional N-linked glycosylation did not cause the second band. In addition, PNGase treatment of full-length ulinastatin confirms that the doublet modification only occurs in the mature ulinastatin sample, not the full-length ulinastatin sample.

Figure 5:
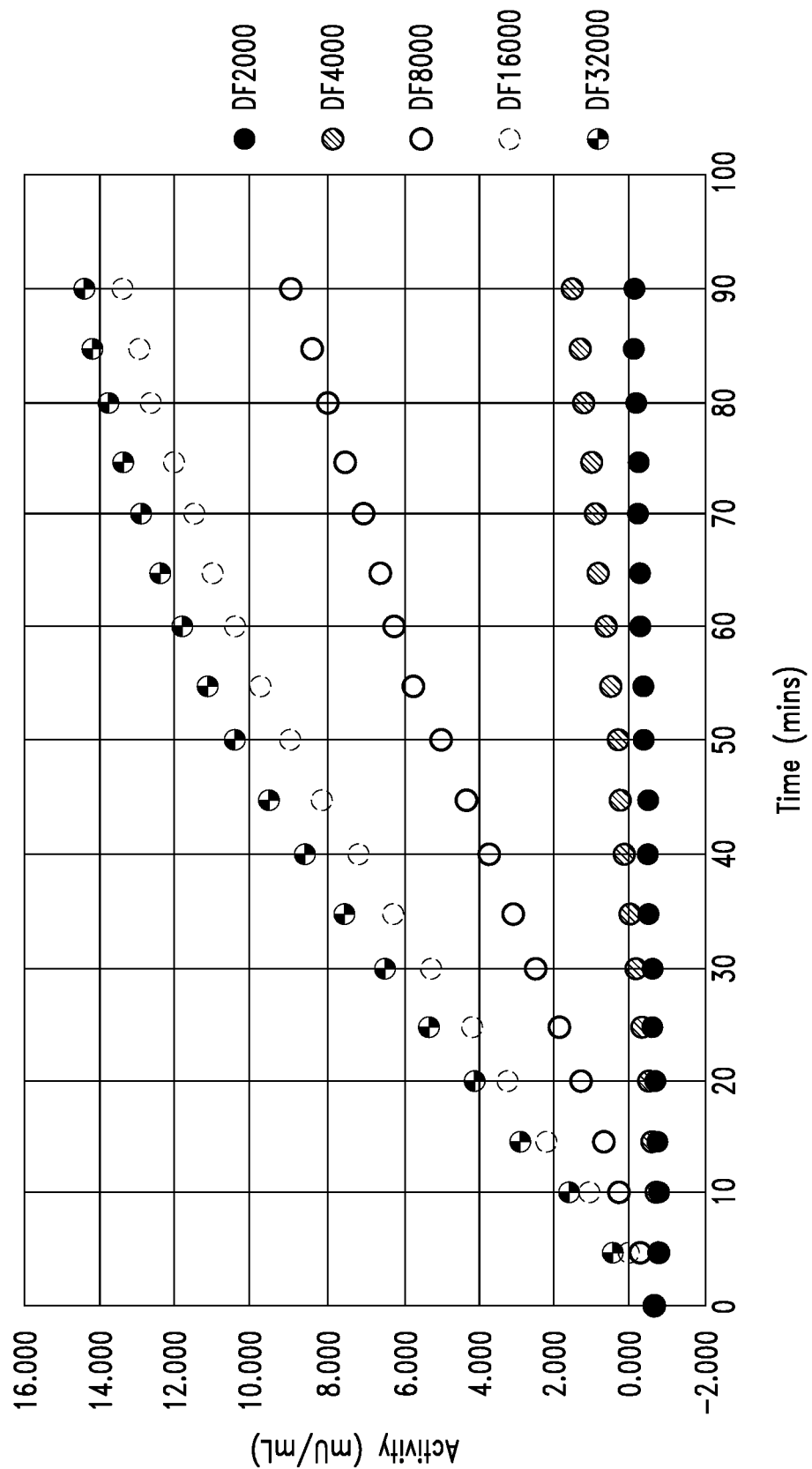
FIG. 5 shows that recombinant ulinastatin polypeptide (T17) inhibits trypsin in vitro. Complete inhibition of trypsin is shown at dilution factor (DF) 200 and 4000. Trypsin inhibitory activity decreased as the dilution factor of ulinastatin increased, evidencing specific inhibitor activity against trypsin.

The mature ulinastatin sample was peptide mapped to determine if the doublet was caused by a variant protein sequence, or another modification to the protein structure. The analysis not only confirmed that there were no modifications to the mature ulinastatin sequence, but surprisingly showed that the upper band in the mature ulinastatin sample is caused by an otherwise non-natural 0-linked glycosylation at threonine 17 (T17). This O-linked glycosylation is not present in the full-length ulinastatin/bovine alpha-lactalbumin signal peptide fusion protein preparation, even after in situ enzyme (furin) cleavage of the full-length ulinastatin to produce the mature form of ulinastatin. It only occurs in mature ulinastatin/bovine alpha-lactalbumin signal peptide fusion protein preparation. The material comprising the mature ulinastatin with the N-linked glycosylation and the unexpected O-linked glycosylation at T17 was tested and found to inhibit trypsin in vitro (see FIG. 5). Here, the trypsin inhibitory activity was analyzed using the Trypsin Activity kit from BioVision™. Dilutions were performed with a sample containing about 5000 U/mg of the recombinant ulinastatin (T17) at a dilution factor (DF) of DF2000, DF4000, DF8000, DF16000, and DF32000.

Example 2

Activity of Recombinant Ulinastatin in Mouse Model of Sepsis

Studies were performed to assess the efficacy of recombinant ulinastatin (see Example 1; 0-linked glycosylation at T17) in a septic mouse model. Male C57BL|6 mice underwent cecal ligation and puncture (CLP) surgery to induce mild-moderate grade sepsis. The study schedule is shown in Table E3.

TABLE E3

Study Schedule

| Grp | n | CLP Grade | Treatment | Total Daily Dose | Dosing Schedule | ROA | Study Endpoint |
|---|---|---|---|---|---|---|---|
| 1 | 10 | Mild-Mod | PBS | 0.1 mL | QD Days 0-4 | IV | 6 Day Survival |
| 2 | 10 | Mild-Mod | Imipenem | 25 mg kg | BID Days 0-4 | SC | 6 Day Survival |
| 3 | 10 | Mild-Mod | R.Ulin | 50,000 U/kg | QD Days 0-4 | IV | 6 Day Survival |
| 4 | 10 | Mild-Mod | R.Ulin | 125,000 U/kg | QD Days 0-4 | IV | 6 Day Survival |
| 5 | 10 | Mild-Mod | R.Ulin | 250,000 U/kg | QD Days 0-4 | IV | 6 Day Survival |

Thirty (30) minutes following surgery, mice were administered the ulinastatin test article, the negative control (phosphate buffered saline, PBS) via intravenous (1V) injection once daily from Day 0 through Day 4, or the positive control imipenem twice daily via subcutaneous (SC) injection from Day 0 through Day 4. Animal survival was tracked for 6 days following CLP surgery and efficacy of test article was determined by comparison of survival between the test article and the negative control.

Figure 6A:
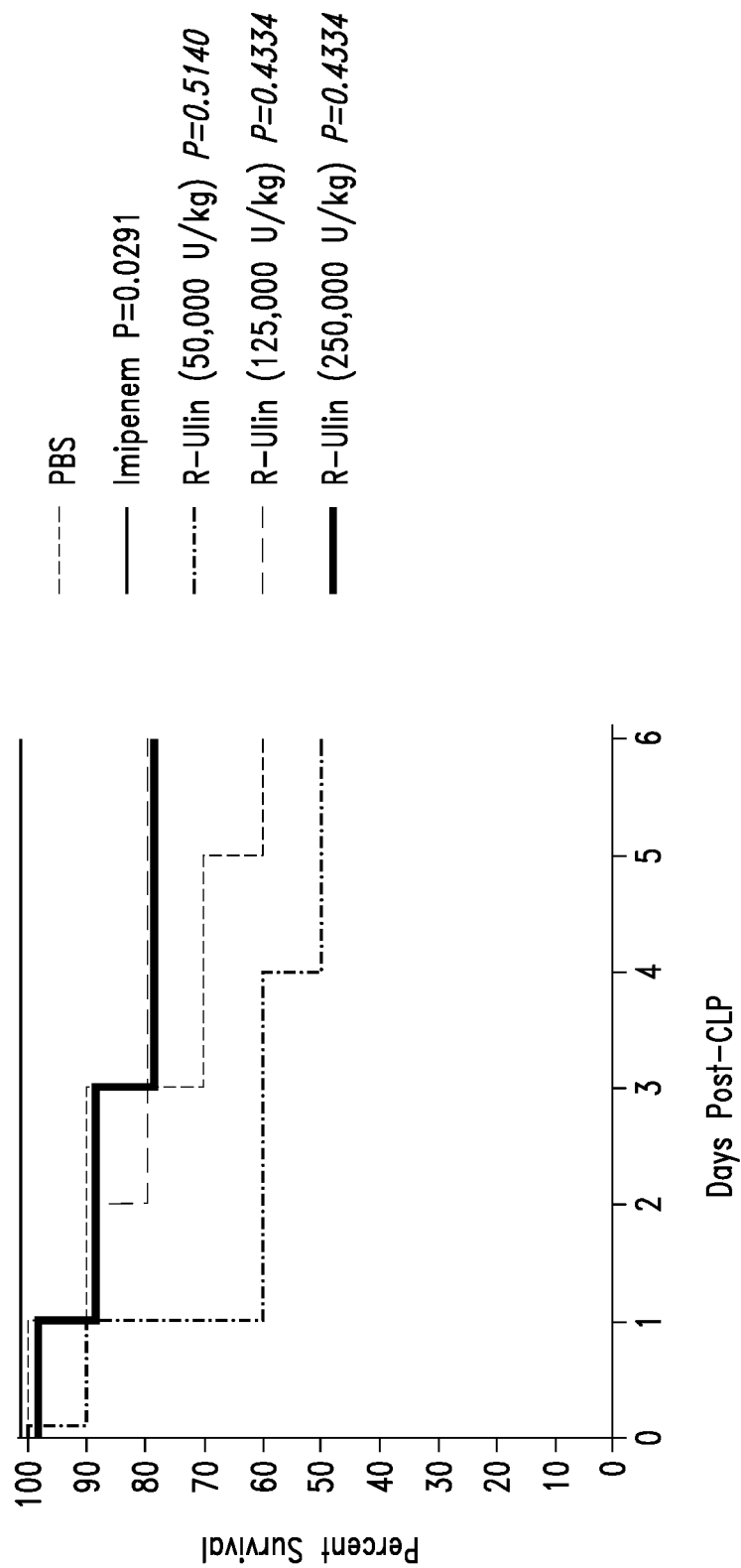
FIGS. 6A-6B show that single doses of recombinant ulinastatin polypeptide (T17) reduced deaths in a dose-dependent manner in a mouse model of sepsis.
Figure 6B:
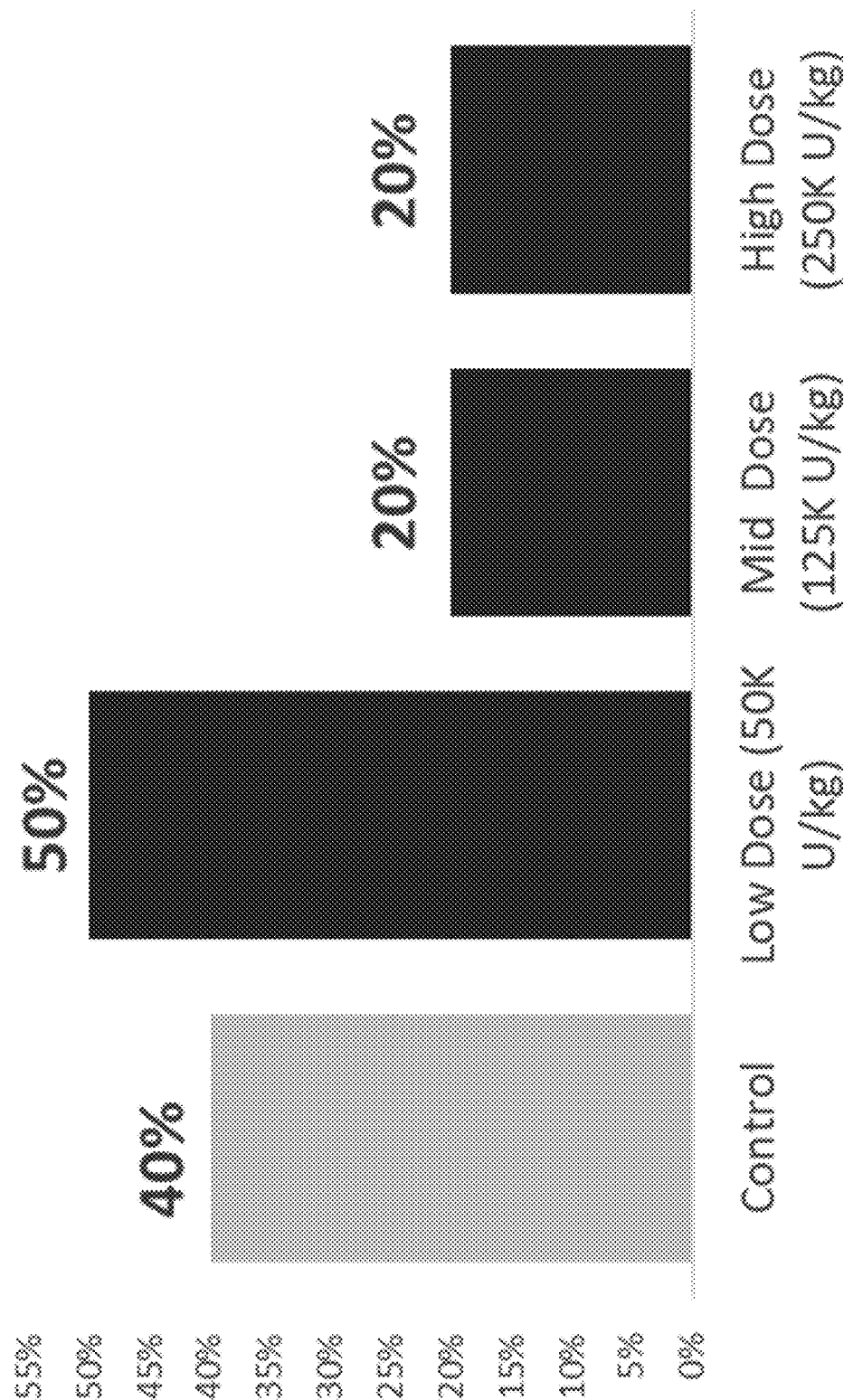

The data are shown in FIGS. 6A-6B. Together, the data demonstrate that cecal ligation and puncture using 22-gauge needle caused a septic infection in male C57BL|6 mice. The PBS vehicle CLP group developed mild-moderate grade sepsis with a 40% death rate, and imipenem treated mice had a 0% death rate, which is within the range observed in previous studies. There was a dose response observed in the recombinant ulinastatin treated groups, with the lowest concentration (50,000 U/kg) having a 50% death rate, and the higher concentrations tested (125,000 and 250,000 U/kg) having only a 20% death rate.

Example 3

Activity of Recombinant Ulinastatin in a Mouse Model of Acute Pancreatitis

Experiments were performed to evaluate the activity of recombinant ulinastatin (T17) at three dose levels in the caerulein-induced acute pancreatitis model in mice.

Acute pancreatitis in male ICR mice was induced by intraperitoneal (IP) injection of caerulein (100 μg/kg) three times at two hour intervals. Test article or vehicle (Sterile PBS) was administered intravenously (IV) at one hour after each caerulein challenge (a total of 3 doses). The reference compound, Devazepide, was administered orally (PO) at one hour after each caerulein challenge. Mice were sacrificed nine hours after the first caerulein challenge. Blood was collected, and serum α-amylase and lipase were detected by an automatic analyzer (TBA-120 FR, Toshiba, Japan).

Figure 7:
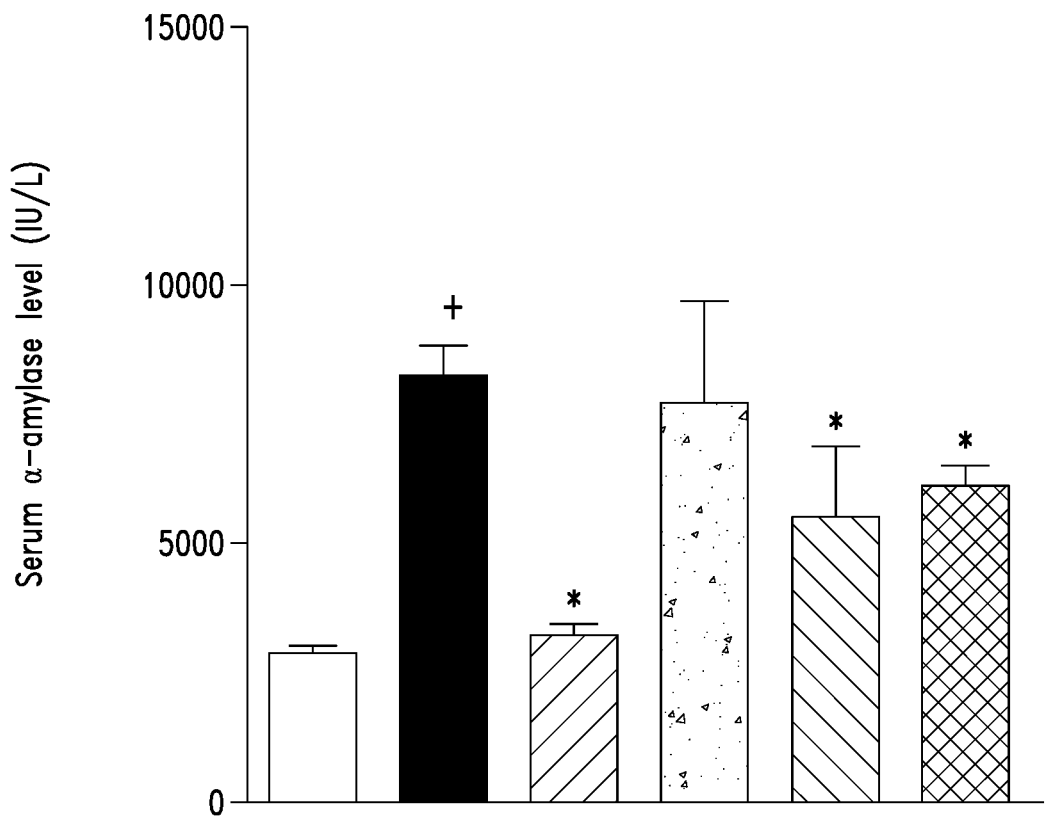
FIG. 7 shows the effects of recombinant ulinastatin on serum α-amylase levels (32% reduction) in a mouse model of acute pancreatitis.
Figure 8:
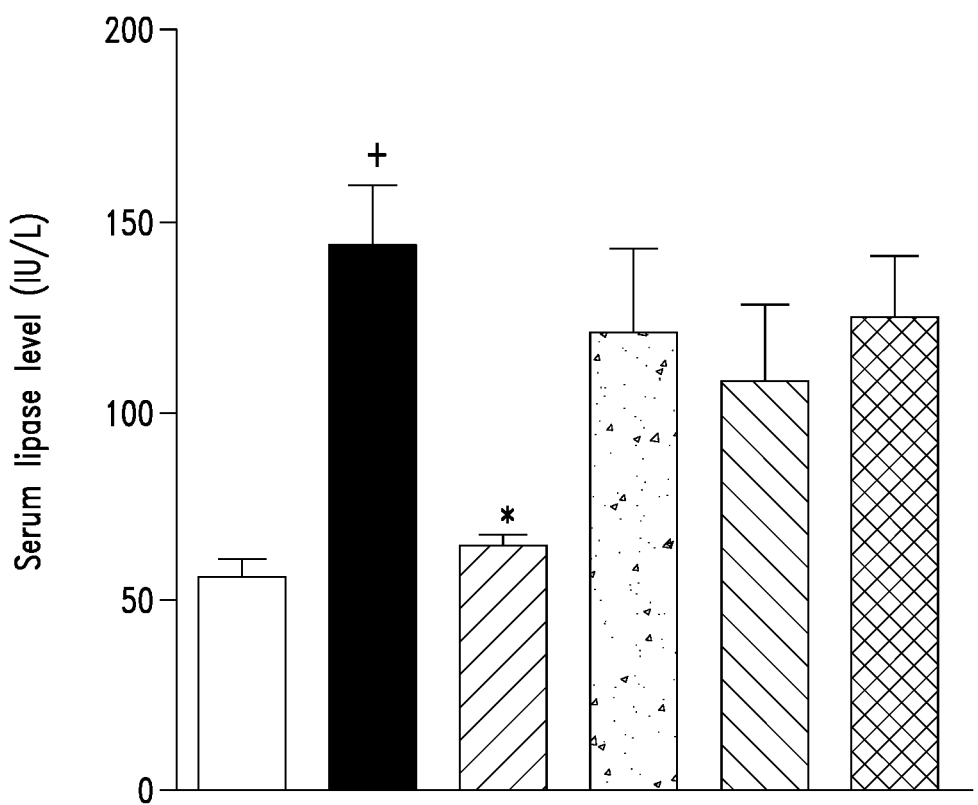
FIG. 8 shows the effects of recombinant ulinastatin on serum lipase levels (25% reduction) in a mouse model of acute pancreatitis.

The results are summarized in FIGS. 7-8 and Table E4 below.

TABLE E4

| Treatment | Dose | Serum Parameter | |
|---|---|---|---|
| | | α-Amylase (IU/L) | Lipase (IU/L) |
| Normal control (Sterile PBS) | 10 mL/kg × 3, IV | 2876.7 ± 106.3 | 57.0 ± 3.5 |
| Vehicle control (Sterile PBS) | 10 mL/kg × 3, IV | 8155.0† ± 614.3 | 142.0† ± 17.3 |
| Devazepide | 0.1 mg/kg × 3, PO | 3225.0* ± 183.6 | 64.0* ± 2.0 |
| R-Ulin | 3.3 mg/kg × 3, PO (16,667 U/kg × 3 = 50,000 U/kg total) | 7695.0 ± 702.0 | 120.3 ± 7.9 |
| R-Ulin | 16.5 mg/kg × 3, PO (83,333 U/kg × 3 = 250,000 U/kg total) | 5480.0* ± 490.8 | 107.3 ± 7.2 |
| R-Ulin | 33 mg/kg × 3, PO (166,667 U/kg × 3 = 500,000 U/kg total) | 6077.5* ± 428.5 | 124.0 ± 16.9 |

One-way ANOVA followed by Dunnett's test was applied for comparison between the treated and vehicle groups. Differences are considered significant †p < 0.05, vs. normal control; *p < 0.05, vs. vehicle control.

Serum α-amylase and lipase, indicators of acute pancreatitis, were significantly ($p<0.05$) increased by repeated caerulein challenges compared to the normal control group, indicating a successful induction of acute pancreatitis in vehicle group at nine hours after first caerulein injection. Oral administrations of Devazepide, the positive control, at 0.1 mg/kg×3 significantly ($p<0.05$) reduced the levels of serum α-amylase and lipase at nine hours after first caerulein injection, when compared to the vehicle group.

Test article (recombinant ulinastatin; T17) given at 16.5 mg/kg×3 (83,333 U/kg×3=250,000 U/kg total) and 33 mg/kg×3 (166,667 U/kg×3=500,000 U/kg total) by oral gavage showed significant ($p<0.05$) decrease in serum α-amylase level at nine hours after first caerulein injection, when compared to the vehicle group. There was a small effect in serum lipase at all 3 dose levels of recombinant ulinastatin compared to the vehicle group.

At the end of the study, the pancreatic samples of all animals were harvested in RNAlater. Quantitative real-time PCR biomarker analysis was performed in pancreas samples. Each assay was run on an Applied Biosystems 7900HT Real-Time PCR system in triplicates and expression fold-changes were derived using the comparative CT method, with GAPDH as endogenous control and sample "1-1" as calibrator. Final results were expressed as the n-fold difference or relative quantification (RQ) in gene expression and RQ of the control sample was always equal to 1.

Figure 9:
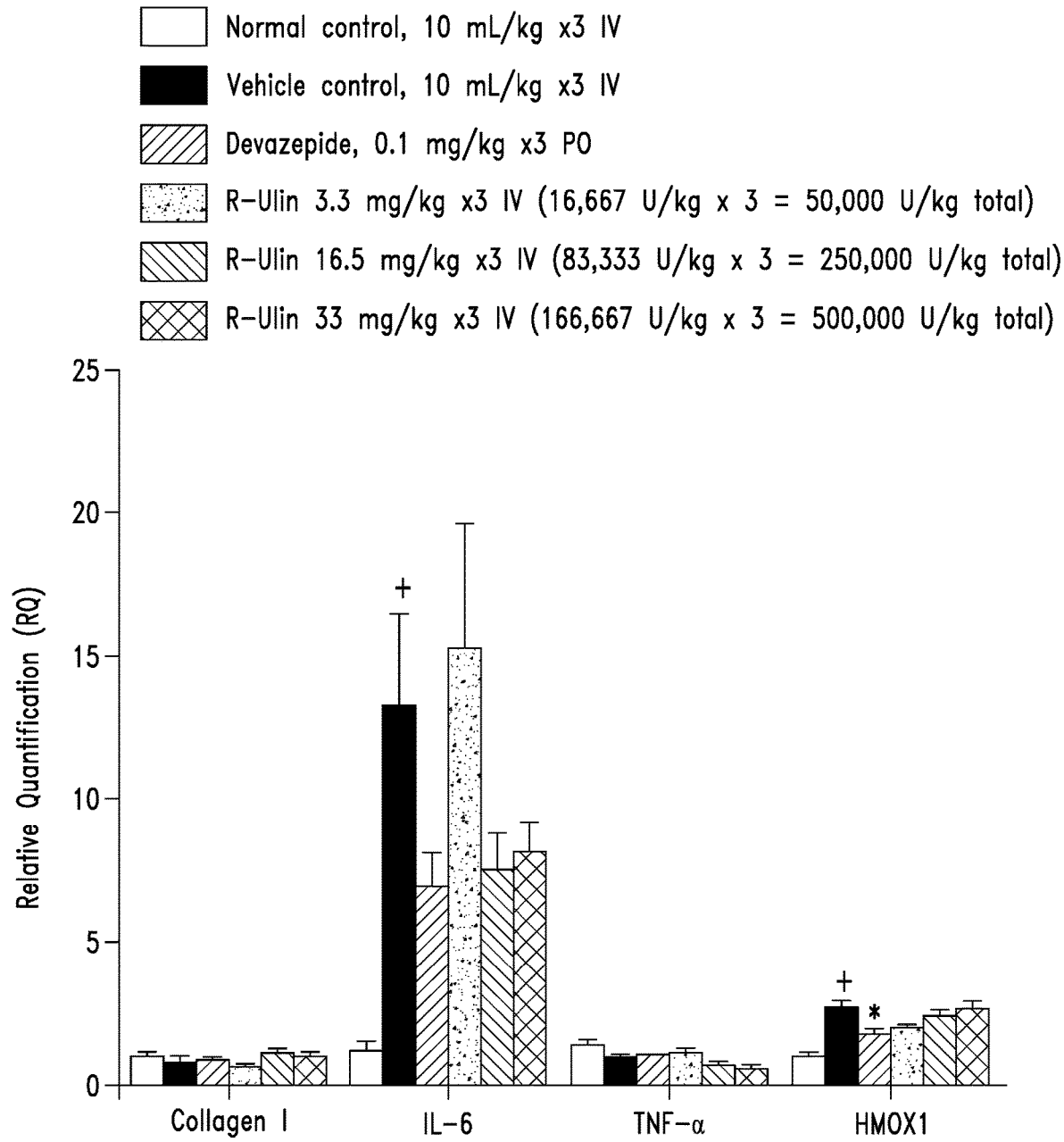
FIG. 9 shows the effects of recombinant ulinastatin on genetic markers of inflammation and oxidative stress in a mouse model of acute pancreatitis.

As shown in FIG. 9, the genetic markers of inflammation (IL-6) and oxidative stress (HMOX1) mRNA levels were significantly ($p<0.05$) increased by repeated caerulein challenges, when compared to the normal control group. Oral administrations of Devazepide at 0.1 mg/kg×3 moderately attenuated IL-6 mRNA expression and significantly ($p<0.05$) attenuated HMOX1 mRNA expression, when compare to vehicle group. Recombinant ulinastatin (T17) given at 16.5 mg/kg×3 PO (83,333 U/kg×3=250,000 U/kg total) and 33 mg/kg×3 PO (166,667 U/kg×3=500,000 U/kg total) attenuated IL-6 mRNA expression, when compare to vehicle group. Recombinant ulinastatin given at 3.3 mg/kg×3 PO (16,667 U/kg×3=50,000 U/kg total), 16.5 mg/kg×3 PO (83,333 U/kg×3=250,000 U/kg total) and 33 mg/kg×3 PO (166,667 U/kg×3=500,000 U/kg total) showed an inverse dose-response in HMOX1 mRNA expression compared to the vehicle group. Collagen I levels were also restored to normal control levels by treatment with recombinant ulinastatin.

Overall, the recombinant ulinastatin given at 16.5 mg/kg×3 PO (83,333 U/kg×3=250,000 U/kg total) and 33 mg/kg×3 PO (166,667 U/kg×3=500,000 U/kg total) significantly decreased serum α-amylase level, and had a notable effect on serum lipase levels, IL-6 mRNA expression, and restoring collagen I levels at nine hours after first caerulein injection in the mouse acute pancreatitis model.

The invention claimed is:

1. An isolated, mature ulinastatin polypeptide, comprising (i) a modified O-linked glycosylation site at residues Glu-Gly-Ser-Gly (SEQ ID NO: 10) which reduces glycosylation at the O-linked glycosylation site, (ii) an N-linked glycan at residue at residue N45, and (iii) an O-linked glycan at residue T17, the residues being defined by SEQ ID NO: 2 or 4, wherein the ulinastatin polypeptide has at least one ulinastatin activity.

2. The isolated, mature ulinastatin polypeptide of claim 1, which comprises or consists of an amino acid sequence that is at least 80% identical to SEQ ID NO: 2 or 4, wherein the ulinastatin polypeptide comprises or retains (i) the modified O-linked glycosylation site, (ii) the N-linked glycan at residue at residue N45, and (iii) the O-linked glycan at residue T17, wherein the ulinastatin polypeptide has at least one ulinastatin activity.

3. The isolated, mature ulinastatin polypeptide of claim 2, which comprises or consists of an amino acid sequence that is at least 80% identical to SEQ ID NO: 2, wherein the ulinastatin polypeptide comprises or retains (i) the S10A substitution of SEQ ID NO: 2, (ii) the N-linked glycan at residue at residue N45, and (iii) the O-linked glycan at residue T17, wherein the ulinastatin polypeptide has at least one ulinastatin activity.

4. The isolated, mature ulinastatin polypeptide of claim 2, which comprises or consists of SEQ ID NO: 2, and comprises the N-linked glycan at residue at residue N45 and the O-linked glycan at residue T17.

5. The isolated, mature ulinastatin polypeptide of claim 1, wherein the at least one ulinastatin activity is selected from one or more of protease inhibitor activities, anti-inflammatory activities, and anti-metastatic activities.

6. The isolated, mature ulinastatin polypeptide of claim 1, wherein the ulinastatin polypeptide has a specific activity of at least about 1000 U/mg, wherein one unit (U) is an amount of the ulinastatin polypeptide that inhibits the activity of 2 μg trypsin by 50%.

7. A therapeutic composition, comprising the isolated, mature ulinastatin polypeptide according to claim 1, and a pharmaceutically-acceptable carrier.

8. A therapeutic composition, comprising a mixture of (a) the isolated, mature ulinastatin polypeptide according to claim 1, and (b) a second, mature ulinastatin polypeptide that comprises an N-linked glycan at residue N45 and does not comprise an O-linked glycan at residue T17, wherein (a) and (b) have at least one ulinastatin activity.

9. The therapeutic of claim 8, wherein (b) comprises a modified O-linked glycosylation site at residues Glu-Gly-Ser-Gly (SEQ ID NO: 10) which reduces glycosylation at the O-linked glycosylation site, and has at least one ulinastatin activity.

10. The therapeutic composition of claim 9, wherein (b) comprises or consists of an amino acid sequence that is at least 80% identical to SEQ ID NO: 2 or 4, comprises or retains the modified O-linked glycosylation site and the N-linked glycan at residue N45, does not comprise the O-linked glycan at residue T17, and has at least one ulinastatin activity.

11. The therapeutic composition of claim 10, wherein (b) comprises or consists of an amino acid sequence that is at least 80% identical to SEQ ID NO: 2, comprises or retains the S10A substitution of SEQ ID NO: 2 and the N-linked glycan at residue N45, does not comprise the O-linked glycan at residue T17, and has at least one ulinastatin activity.

12. The therapeutic composition of claim 11, wherein (b) comprises or consists of SEQ ID NO: 2, comprises the N-linked glycan at residue N45, does not comprise the O-linked glycan at residue T17, and has at least one ulinastatin activity.

13. The therapeutic composition of claim 8, wherein (a):(b) are present in the composition at a ratio ranging from about 20:1 to about 1:20.

14. The therapeutic composition of claim 7, which is substantially free of other glycosylated isoforms (glycoforms) of ulinastatin.

15. The therapeutic composition of claim 7, which has endotoxin levels of less than about 1 EU/mg protein, host cell protein of less than about 100 ng/mg total protein, host cell DNA of less than about 10 pg/mg total protein, and/or is substantially aggregate-free.

16. A method of treating an inflammatory disease or condition in a subject in need thereof, comprising administering to the subject a therapeutic composition of claim 7, thereby treating the inflammatory disease or condition in the subject.

17. The method of claim 16, wherein the inflammatory disease or condition is selected from one or more of pancreatitis, systemic inflammation, colitis, autoimmune encephalomyelitis, Stevens-Johnson syndrome, arthritis, renal failure, burns, sepsis/septic shock including severe sepsis and related pro-inflammatory/secondary conditions, systemic inflammatory response syndrome (SIRS), toxic epidermal necrolysis (TEN), Kawasaki disease, kidney disease, ischemic conditions, lung inflammation and inflammatory lung conditions, liver inflammation including hepatitis, anaphylaxis, post-operative or post-surgical complications, lipopolysaccharide (LPS)-induced inflammation or tissue injury, inflammation or dysfunction secondary to diabetes, burn injury, heat stroke, inflammatory or neuropathic pain, acute poisoning, hyperlipidemia-associated inflammation, autoimmunity-associated inflammation, allogeneic transplant or blood transfusion-associated inflammation, neuroinflammation, and cancer-associated inflammation.

18. The method of claim 16, wherein administering the modified ulinastatin polypeptide reduces one or more of protease activity, endothelial activation/damage, proinflammatory cytokine and chemokine production/release (optionally, IL-1β, MIP-1α, MCP-1, and/or CXCL1), fibrinogen synthesis, neutrophil recruitment into organs, and/or organ injury in the subject.

19. A method of treating, ameliorating the symptoms of, or inhibiting the progression of, a cancer in a subject in need thereof, comprising administering to the subject a therapeutic composition of claim 7, thereby treating, ameliorating the symptoms of, or inhibiting the progression of, a cancer in a subject in need thereof.

20. The method of claim 19, wherein the cancer is selected from one or more of melanoma, pancreatic cancer, bone cancer, prostate cancer, small cell lung cancer, non-small cell lung cancer (NSCLC), mesothelioma, leukemia, lymphoma, hepatoma (hepatocellular carcinoma), sarcoma, B-cell malignancy, breast cancer, ovarian cancer, colorectal cancer, glioma, glioblastoma multiforme, meningioma, pituitary adenoma, vestibular schwannoma, primary CNS lymphoma, primitive neuroectodermal tumor (medulloblastoma), kidney cancer, bladder cancer, uterine cancer, esophageal cancer, brain cancer, head and neck cancers, cervical cancer, testicular cancer, thyroid cancer, and stomach cancer.

21. The method of claim 19, wherein the cancer is a metastatic cancer, optionally wherein administering the modified ulinastatin polypeptide reduces cancer cell invasion and/or angiogenesis.

22. The method of claim 21, wherein the metastatic cancer is selected from one or more of:
(a) a bladder cancer which has metastasized to the bone, liver, and/or lungs;
(b) a breast cancer which has metastasized to the bone, brain, liver, and/or lungs;
(c) a colorectal cancer which has metastasized to the liver, lungs, and/or peritoneum;
(d) a kidney cancer which has metastasized to the adrenal glands, bone, brain, liver, and/or lungs;
(e) a lung cancer which has metastasized to the adrenal glands, bone, brain, liver, and/or other lung sites;
(f) a melanoma which has metastasized to the bone, brain, liver, lung, and/or skin/muscle;
(g) an ovarian cancer which has metastasized to the liver, lung, and/or peritoneum;
(h) a pancreatic cancer which has metastasized to the liver, lung, and/or peritoneum;
(i) a prostate cancer which has metastasized to the adrenal glands, bone, liver, and/or lungs;
(j) a stomach cancer which has metastasized to the liver, lung, and/or peritoneum;
(l) a thyroid cancer which has metastasized to the bone, liver, and/or lungs; and
(m) a uterine cancer which has metastasized to the bone, liver, lung, vagina, and/or peritoneum.

23. The therapeutic composition of claim 13, wherein (a):(b) are present in the composition at a ratio of about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10.

24. The method of claim 17, wherein the pancreatitis is selected from acute pancreatitis, chronic pancreatitis, and endoscopic retrograde cholangiopancreatography (ERCP)-induced pancreatitis.

25. The method of claim 17, wherein the kidney disease is selected from acute kidney failure and chronic kidney disease.

26. The method of claim 17, wherein the ischemic condition is an ischemia-reperfusion injury in the liver, kidney, heart, lungs, or brain.

27. The method of claim 17, wherein the inflammatory lung conditions is a pulmonary infection, pneumonia, infectious interstitial pneumonia associated with mixed connective tissue disease, pulmonary fibrosis, or acute respiratory distress syndrome.

* * * * *